US010676523B2

(12) United States Patent
Andre et al.

(10) Patent No.: US 10,676,523 B2
(45) Date of Patent: *Jun. 9, 2020

(54) TREATMENT REGIMENS USING ANTI-NKG2A ANTIBODIES

(71) Applicant: INNATE PHARMA, Marseilles (FR)

(72) Inventors: Pascale Andre, Marseilles (FR); Mathieu Blery, Marseilles (FR); Carine Paturel, Marcy l'Etoile (FR); Caroline Soulas, Marseilles (FR); Nicolaï Wagtmann, Cassis (FR)

(73) Assignee: INNATE PHARMA, Marseilles (FR)

( * ) Notice: Subject to any disclaimer, the term of this patent is extended or adjusted under 35 U.S.C. 154(b) by 266 days.

This patent is subject to a terminal disclaimer.

(21) Appl. No.: 15/511,792

(22) PCT Filed: Sep. 15, 2015

(86) PCT No.: PCT/EP2015/071073
§ 371 (c)(1),
(2) Date: Mar. 16, 2017

(87) PCT Pub. No.: WO2016/041947
PCT Pub. Date: Mar. 24, 2016

(65) Prior Publication Data
US 2017/0298131 A1 Oct. 19, 2017

Related U.S. Application Data

(60) Provisional application No. 62/093,124, filed on Dec. 17, 2014, provisional application No. 62/093,141, filed on Dec. 17, 2014, provisional application No. 62/083,929, filed on Nov. 25, 2014, provisional application No. 62/067,642, filed on Oct. 23, 2014, provisional application No. 62/050,948, filed on Sep. 16, 2014.

(51) Int. Cl.
C07K 16/28 (2006.01)
A61K 39/395 (2006.01)
C07K 16/30 (2006.01)
A61K 39/00 (2006.01)

(52) U.S. Cl.
CPC .... *C07K 16/2803* (2013.01); *A61K 39/39558* (2013.01); *C07K 16/2863* (2013.01); *C07K 16/30* (2013.01); *A61K 2039/505* (2013.01); *A61K 2039/545* (2013.01); *C07K 2317/21* (2013.01); *C07K 2317/24* (2013.01); *C07K 2317/52* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 8,206,709 B2 | 6/2012 | Spee et al. |
| 8,796,427 B2 | 8/2014 | Spee et al. |
| 8,901,283 B2 | 12/2014 | Spee et al. |
| 8,993,319 B2 | 3/2015 | Moretta et al. |
| 9,422,368 B2 | 8/2016 | Spee et al. |
| 9,512,228 B2 | 12/2016 | Soederstroem et al. |
| 9,683,041 B2 | 6/2017 | Spee et al. |
| 10,160,810 B2 | 12/2018 | Moretta et al. |
| 2003/0095965 A1 | 5/2003 | Van Beneden et al. |
| 2017/0073417 A1 | 3/2017 | Soederstroem et al. |
| 2017/0281809 A1 | 10/2017 | Spee et al. |
| 2017/0291947 A1 | 10/2017 | Andre et al. |
| 2017/0313773 A1 | 11/2017 | Andre et al. |
| 2019/0031755 A1 | 1/2019 | Andre et al. |

FOREIGN PATENT DOCUMENTS

| WO | WO 99/28748 | 6/1999 |
| WO | WO 2006/070286 | 7/2006 |
| WO | WO 2008/009545 | 1/2008 |
| WO | WO 2009/092805 | 7/2009 |
| WO | WO 2012/172102 | 12/2012 |
| WO | WO 2016/041945 | 3/2016 |

OTHER PUBLICATIONS

Pitt et al (I, 44:1255-1269, 2016).*
Creelan et al (NRCO: 16:277-278, 2019).*
Lloyd et al (Protein Engineering, Design & Selection, 22:159-168, 2009).*
Edwards et al (J Mol Biol, 14;334(1):103-118, 2003).*
Claims as filed for U.S. Appl. No. 16/226,742, 2018, pp. 1-3.
Coupel, S. et al. "Expression and release of soluble HLA-E is an immunoregulatory feature of endothelial cell activation" *Blood*, Apr. 1, 2007, pp. 2806-2814, vol. 109, No. 7.
Derre, L. et al. "Expression and Release of HLA-E by Melanoma Cells and Melanocytes: Potential Impact on the Response of Cytotoxic Effector Cells" *The Journal of Immunology*, 2006, pp. 3100-3107, vol. 177.

(Continued)

*Primary Examiner* — Brad Duffy
(74) *Attorney, Agent, or Firm* — Saliwanchik, Lloyd & Eisenschenk

(57) ABSTRACT

The present invention relates to methods for the treatment of disease, notably cancer, using antibodies that specifically bind and inhibit human NKG2A. Included are therapeutic regimens that provide improved efficacy of anti-NKG2A antibodies.

10 Claims, 10 Drawing Sheets
Specification includes a Sequence Listing.

(56) References Cited

OTHER PUBLICATIONS

Written Opinion in International Application No. PCT/EP2015/071073, dated Dec. 21, 2015, pp. 1-6.
Lloyd, P. "Challenges in early clinical development of biologics" Mar. 1, 2011, pp. 1-37, retrieved from the Internet: URL:http://www.pharma.be/assets/files/2309/2309_129520955506916441.pdf on Dec. 3, 2012, XP055233283.
Innate Pharma [online], "R&D Update" Apr. 10, 2014, pp. 1-108, retrieved from the Internet: URL:http://innate-pharma.com/sites/default/files/140410_rd_day_final_0.pdf on Dec. 1, 2015, XP0055232714.

* cited by examiner

SEQUENCE LISTING

```
<160> NUMBER OF SEQ ID NOS: 15

<210> SEQ ID NO 1
<211> LENGTH: 233
<212> TYPE: PRT
<213> ORGANISM: Homo sapiens

<400> SEQUENCE: 1

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
```

Ile Ile Tyr His Cys Lys His Lys Leu
225                 230

<210> SEQ ID NO 2
<211> LENGTH: 452
<212> TYPE: PRT
<213> ORGANISM: Artificial
<220> FEATURE:
<223> OTHER INFORMATION: Chimeric mouse-human

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Met Asn Trp Val Arg Gln Met Pro Gly Lys Gly Leu Glu Trp Met
            35                  40                  45

Gly Arg Ile Asp Pro Tyr Asp Ser Glu Thr His Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln

```
                    340                 345                 350
Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 3
<211> LENGTH: 452
<212> TYPE: PRT
<213> ORGANISM: Artificial
<220> FEATURE:
<223> OTHER INFORMATION: Chimeric mouse-human

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
```

```
                245                 250                 255
Met Ile Ser Arg Thr Pro Glu Val Thr Cys Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Gln Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Leu Gly Lys
    450

<210> SEQ ID NO 4
<211> LENGTH: 452
<212> TYPE: PRT
<213> ORGANISM: Artificial
<220> FEATURE:
<223> OTHER INFORMATION: Chimeric mouse-human

<400> SEQUENCE: 4

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
```

```
            145                 150                 155                 160
        Pro Val Thr Val Ser Trp Asn Ser Gly Ala Leu Thr Ser Gly Val His
                        165                 170                 175

Thr Phe Pro Ala Val Leu Gln Ser Ser Gly Leu Tyr Ser Leu Ser Ser
                        180                 185                 190

Val Val Thr Val Pro Ser Ser Leu Gly Thr Lys Thr Tyr Thr Cys
                        195                 200                 205

Asn Val Asp His Lys Pro Ser Asn Thr Lys Val Asp Lys Arg Val Glu
                        210                 215                 220

Ser Lys Tyr Gly Pro Pro Cys Pro Pro Cys Pro Ala Pro Glu Phe Leu
        225                 230                 235                 240

Gly Gly Pro Ser Val Phe Leu Phe Pro Pro Lys Pro Lys Asp Thr Leu
                        245                 250                 255

Met Ile Ser Arg Thr Pro Glu Val Thr Cys Val Val Val Asp Val Ser
                        260                 265                 270

Gln Glu Asp Pro Glu Val Gln Phe Asn Trp Tyr Val Asp Gly Val Glu
                        275                 280                 285

Val His Asn Ala Lys Thr Lys Pro Arg Glu Glu Gln Phe Asn Ser Thr
                        290                 295                 300

Tyr Arg Val Val Ser Val Leu Thr Val Leu His Gln Asp Trp Leu Asn
        305                 310                 315                 320

Gly Lys Glu Tyr Lys Cys Lys Val Ser Asn Lys Gly Leu Pro Ser Ser
                        325                 330                 335

Ile Glu Lys Thr Ile Ser Lys Ala Lys Gly Gln Pro Arg Glu Pro Gln
                        340                 345                 350

Val Tyr Thr Leu Pro Pro Ser Gln Glu Glu Met Thr Lys Asn Gln Val
                        355                 360                 365

Ser Leu Thr Cys Leu Val Lys Gly Phe Tyr Pro Ser Asp Ile Ala Val
                        370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Arg Leu Thr
                        405                 410                 415

Val Asp Lys Ser Arg Trp Gln Glu Gly Asn Val Phe Ser Cys Ser Val
                        420                 425                 430

Met His Glu Ala Leu His Asn His Tyr Thr Gln Lys Ser Leu Ser Leu
                        435                 440                 445

Ser Leu Gly Lys
            450

<210> SEQ ID NO 5
<211> LENGTH: 452
<212> TYPE: PRT
<213> ORGANISM: Artificial
<220> FEATURE:
<223> OTHER INFORMATION: Chimeric mouse-human

<400> SEQUENCE: 5

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
                20                  25                  30

Trp Met Asn Trp Val Gln Gln Ala Pro Gly Lys Gly Leu Glu Trp Met
            35                  40                  45

Gly Arg Ile Asp Pro Tyr Asp Ser Glu Thr His Tyr Ala Glu Lys Phe
```

```
              50                  55                  60
Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                     85                  90                  95

Ala Thr Gly Gly Tyr Asp Phe Asp Val Gly Thr Leu Tyr Trp Phe Phe
                100                 105                 110

Asp Val Trp Gly Gln Gly Thr Thr Val Thr Val Ser Ser Ala Ser Thr
                115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
                195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
                275                 280                 285

Val His Asn Ala Lys Thr Lys Pro Arg Glu Glu Gln Phe Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
                435                 440                 445

Ser Leu Gly Lys
            450
```

<210> SEQ ID NO 6

```
<211> LENGTH: 452
<212> TYPE: PRT
<213> ORGANISM: Artificial
<220> FEATURE:
<223> OTHER INFORMATION: Chimeric mouse-human

<400> SEQUENCE: 6
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Trp | Met | Asn | Trp | Val | Arg | Gln | Ala | Pro | Gly | Gln | Gly | Leu | Glu | Trp | Met |
| | | | 35 | | | | | 40 | | | | | 45 | | |
| Gly | Arg | Ile | Asp | Pro | Tyr | Asp | Ser | Glu | Thr | His | Tyr | Ala | Gln | Lys | Phe |
| | 50 | | | | | 55 | | | | | 60 | | | | |
| Gln | Gly | Arg | Val | Thr | Met | Thr | Arg | Asp | Thr | Ser | Thr | Ser | Thr | Val | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Gly | Tyr | Asp | Phe | Asp | Val | Gly | Thr | Leu | Tyr | Trp | Phe | Phe |
| | | | 100 | | | | | 105 | | | | | 110 | | |
| Asp | Val | Trp | Gly | Gln | Gly | Thr | Thr | Val | Thr | Val | Ser | Ser | Ala | Ser | Thr |
| | | | 115 | | | | | 120 | | | | | 125 | | |
| Lys | Gly | Pro | Ser | Val | Phe | Pro | Leu | Ala | Pro | Cys | Ser | Arg | Ser | Thr | Ser |
| | 130 | | | | | 135 | | | | | 140 | | | | |
| Glu | Ser | Thr | Ala | Ala | Leu | Gly | Cys | Leu | Val | Lys | Asp | Tyr | Phe | Pro | Glu |
| 145 | | | | | 150 | | | | | 155 | | | | | 160 |
| Pro | Val | Thr | Val | Ser | Trp | Asn | Ser | Gly | Ala | Leu | Thr | Ser | Gly | Val | His |
| | | | | 165 | | | | | 170 | | | | | 175 | |
| Thr | Phe | Pro | Ala | Val | Leu | Gln | Ser | Ser | Gly | Leu | Tyr | Ser | Leu | Ser | Ser |
| | | | 180 | | | | | 185 | | | | | 190 | | |
| Val | Val | Thr | Val | Pro | Ser | Ser | Ser | Leu | Gly | Thr | Lys | Thr | Tyr | Thr | Cys |
| | | | 195 | | | | | 200 | | | | | 205 | | |
| Asn | Val | Asp | His | Lys | Pro | Ser | Asn | Thr | Lys | Val | Asp | Lys | Arg | Val | Glu |
| | 210 | | | | | 215 | | | | | 220 | | | | |
| Ser | Lys | Tyr | Gly | Pro | Pro | Cys | Pro | Pro | Cys | Pro | Ala | Pro | Glu | Phe | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| Gln | Glu | Asp | Pro | Glu | Val | Gln | Phe | Asn | Trp | Tyr | Val | Asp | Gly | Val | Glu |
| | | | 275 | | | | | 280 | | | | | 285 | | |
| Val | His | Asn | Ala | Lys | Thr | Lys | Pro | Arg | Glu | Glu | Gln | Phe | Asn | Ser | Thr |
| | 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Gly | Leu | Pro | Ser | Ser |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Gln | Glu | Glu | Met | Thr | Lys | Asn | Gln | Val |
| | | | 355 | | | | | 360 | | | | | 365 | | |
| Ser | Leu | Thr | Cys | Leu | Val | Lys | Gly | Phe | Tyr | Pro | Ser | Asp | Ile | Ala | Val |
| | 370 | | | | | 375 | | | | | 380 | | | | |

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 7
<211> LENGTH: 214
<212> TYPE: PRT
<213> ORGANISM: Artificial
<220> FEATURE:
<223> OTHER INFORMATION: Chimeric mouse-human

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 5
<212> TYPE: PRT
<213> ORGANISM: mus musculus

<400> SEQUENCE: 8

Ser Tyr Trp Met Asn
1               5
```

<210> SEQ ID NO 9
<211> LENGTH: 11
<212> TYPE: PRT
<213> ORGANISM: Mus musculus

<400> SEQUENCE: 9

Arg Ile Asp Pro Tyr Asp Ser Glu Thr His Tyr
1               5                   10

<210> SEQ ID NO 10
<211> LENGTH: 17
<212> TYPE: PRT
<213> ORGANISM: Artificial
<220> FEATURE:
<223> OTHER INFORMATION: Chimeric mouse-human

<400> SEQUENCE: 10

Arg Ile Asp Pro Tyr Asp Ser Glu Thr His Tyr Ser Pro Ser Phe Gln
1               5                   10                  15

Gly

<210> SEQ ID NO 11
<211> LENGTH: 17
<212> TYPE: PRT
<213> ORGANISM: Artificial
<220> FEATURE:
<223> OTHER INFORMATION: Chimeric mouse-human

<400> SEQUENCE: 11

Arg Ile Asp Pro Tyr Asp Ser Glu Thr His Tyr Ala Gln Lys Leu Gln
1               5                   10                  15

Gly

<210> SEQ ID NO 12
<211> LENGTH: 16
<212> TYPE: PRT
<213> ORGANISM: Mus musculus

<400> SEQUENCE: 12

Gly Gly Tyr Asp Phe Asp Val Gly Thr Leu Tyr Trp Phe Phe Asp Val
1               5                   10                  15

<210> SEQ ID NO 13
<211> LENGTH: 11
<212> TYPE: PRT
<213> ORGANISM: Mus musculus

<400> SEQUENCE: 13

Arg Ala Ser Glu Asn Ile Tyr Ser Tyr Leu Ala
1               5                   10

<210> SEQ ID NO 14
<211> LENGTH: 7
<212> TYPE: PRT
<213> ORGANISM: Mus musculus

<400> SEQUENCE: 14

Asn Ala Lys Thr Leu Ala Glu
1               5

<210> SEQ ID NO 15
<211> LENGTH: 9
<212> TYPE: PRT
<213> ORGANISM: Mus musculus

```
<400> SEQUENCE: 15

Gln His His Tyr Gly Thr Pro Arg Thr
1               5
```

TREATMENT REGIMENS USING ANTI-NKG2A ANTIBODIES

CROSS-REFERENCE TO RELATED APPLICATIONS

This application is the U.S. national stage application of International Patent Application No. PCT/EP2015/071073, filed Sep. 15, 2015, which claims the benefit of U.S. Provisional Application Nos. 62/050,948, filed Sep. 16, 2014; 62/067,642 filed Oct. 23, 2014; 62/083,929 filed Nov. 25, 2014; 62/093,141 filed Dec. 17, 2014; and 62/093,124 filed Dec. 17, 2014; all of which are incorporated herein by reference in their entirety; including any drawings.

REFERENCE TO SEQUENCE LISTING

The present application is being filed along with a Sequence Listing in electronic format. The Sequence Listing is provided as a file entitled "NKG2A-T_ST25", created Sep. 15, 2015, which is 26 KB in size. The information in the electronic format of the Sequence Listing is incorporated herein by reference in its entirety.

FIELD OF THE INVENTION

This invention relates to the use of anti-NKG2A-antibodies for therapy, notably for the treatment of cancers.

BACKGROUND OF THE INVENTION

NK cell activity is regulated by a complex mechanism that involves both activating and inhibitory signals. Several distinct NK-specific receptors have been identified that play an important role in the NK cell mediated recognition and killing of HLA Class I deficient target cells. Natural Cytotoxicity Receptors (NCR) refers to a class of activating receptor proteins, and the genes expressing them, that are specifically expressed in NK cells. Examples of NCRs include NKp30, NKp44, and NKp46 (see, e.g., Lanier (2001) Nat Immunol 2:23-27, Pende et al. (1999) J Exp Med. 190:1505-1516, Cantoni et al. (1999) J Exp Med. 189:787-796, Sivori et al (1997) J. Exp. Med. 186:1129-1136, Pessino et al. (1998) J Exp Med. 188(5):953-60; Mandelboim et al. (2001) Nature 409:1055-1060, the entire disclosures of which are herein incorporated by reference). These receptors are members of the Ig super-family, and their cross-linking, induced by specific mAbs, leads to a strong NK cell activation resulting in increased intracellular $Ca^{++}$ levels, triggering of cytotoxicity, and lymphokine release, and an activation of NK cytotoxicity against many types of target cells.

CD94/NKG2A is an inhibitory receptor found on subsets of natural killer cells (NK cells), Natural Killer T cells (NKT cells) and T cells ($\alpha/\beta$ and $\gamma/\delta$). CD94/NKG2A restricts cytokine release and cytotoxic responses of aforementioned lymphocytes towards cells expressing the CD94/NKG2A-ligand HLA-E (see, e.g., WO99/28748). HLA-E has also been found to be secreted in soluble form by certain tumor cells (Derre et al., J Immunol 2006; 177:3100-7) and activated endothelial cells (Coupe et al., Blood 2007; 109: 2806-14). Antibodies that inhibit CD94/NKG2A signalling may increase the cytokine release and cytolytic activity of lymphocytes towards HLA-E positive target cells, such as responses of CD94/NKG2A-positive NK cells responses towards virally infected cells. Therefore, therapeutic antibodies that inhibit CD94/NKG2A but that do not provoke the killing of CD94/NKG2A-expressing cells (i.e. non-depleting antibodies), may induce control of tumor-growth in cancer patients. In addition, anti-NKG2A antibodies have also been suggested for use in treating autoimmune or inflammatory diseases (see, e.g., US20030095965, WO2006070286).

Various antibodies against NKG2A have been described in the art. WO2006070286 and U.S. Pat. No. 8,206,709 (see also WO2008/009545) describe anti-NKG2A antibody Z270, while WO2009/092805 describes humanized anti-NKG2A antibody Z199. Vance et al. (J Exp Med 1999; 190: 1801-12) refers to rat anti-murine NKG2-antibody 20D5 (now commercially available via BD Biosciences Pharmingen, Catalog No. 550518, USA); and U.S. patent application publication 20030095965 describes murine antibody 3S9. Antibody Z270 binds and neutralizes the inhibitory receptor NKG2A without neutralizing the activating receptors NKG2C and NKG2E. Antibody Z199, 20D5 and 3S9 all bind the activating NKG2 family members NKG2C and NKG2E in addition to NKG2A. Antibody Z270 blocks the binding of HLA-E to NKG2A, while antibody Z199 neutralises NKG2A without interfering with the binding of NKG2A to H LA-E.

SUMMARY OF THE INVENTION

The present inventors have discovered that doses and concentrations of anti-NKG2A antibody that fully occupy NKG2A receptors on lymphocytes do not yield maximal neutralization of NKG2A receptors in the presence of HLA-E expressing target cells in vivo. In particular, the concentration of anti-NKG2A antibody required for full neutralization of NKG2A receptors on NK cells in the presence of HLA-E expressing target cells is 100-fold higher than the concentration observed to fully occupy NKG2A receptors in binding assays using NKG2A+ lymphocytes. In parallel, it is observed that the anti-tumor effect of anti-NKG2A is increased as a function of higher expression of HLA-E on tumor cells.

As shown herein NKG2A+ NK and CD8+ T lymphocytes are present not only in circulation but within the tumor environment, and NKG2A+ CD8 T cells may furthermore be found at significantly increased frequencies within the tumor-infiltrating subset, compared to CD8+ T cells in tumor draining lymph nodes and spleen. The treatment regimens of the invention therefore additionally provide advantageous methods for treating solid tumors by using anti-NKG2A antibodies to modulate lymphocytes within the tumor environment.

In one embodiment, provided is a method for treating or preventing a disease (e.g. a cancer, a solid tumor, a hematological tumor) in an individual, the method comprising administering to an individual having disease (e.g. a cancer, a solid tumor) an antibody that neutralizes the inhibitory activity of a human NKG2A polypeptide, wherein the anti-NKG2A antibody is administered in an amount effective to achieve a blood (serum) concentration of anti-NKG2A antibody that corresponds to at least the $EC_{50}$, optionally the $EC_{100}$, for NKG2A+ NK cell response. In one embodiment, the amount is effective to achieve a concentration in extravascular tissue (e.g. tumor tissue) of anti-NKG2A antibody that corresponds to at least the $EC_{50}$, optionally the $EC_{100}$, for NKG2A+ NK cell response. In one embodiment, NKG2A+ NK cell response is assessed using an assay of cytotoxic activity of NKG2A-expressing NK cells toward HLA-E expressing target cells.

In one embodiment, provided is a method for treating or preventing a disease (e.g. a cancer, a solid tumor, a hematological tumor) in an individual, the method comprising administering to an individual having disease (e.g. a cancer, a solid tumor) an antibody that neutralizes the inhibitory activity of a human NKG2A polypeptide, wherein the anti-NKG2A antibody is administered in an amount effective to achieve (and/or to maintain for a specified period of time or between two successive administrations) a blood (serum) concentration of anti-NKG2A antibody of at least 10 µg/ml (or, optionally at least 20, 30, 40, 50, 80 or 100 µg/mL).

Accordingly, in one embodiment, provided is a method for treating or preventing a disease (e.g. a cancer, a solid tumor, a hematological tumor) in an individual, the method comprising administering to an individual an antibody that binds NKG2A and that neutralizes the inhibitory activity of a human NKG2A polypeptide for at least one administration cycle, the administration cycle comprising at least a first and second (and optionally a $3^{rd}$, $4^{th}$, $5^{th}$, $6^{th}$, $7^{th}$ and/or $8^{th}$ or further) administration of the anti-NKG2A antibody, wherein the anti-NKG2A antibody is administered in an amount effective to achieve blood concentration of anti-NKG2A antibody, and/or to maintain blood concentration of anti-NKG2A antibody between two successive (e.g. said first and second, and optionally the further) administrations, which concentration is at least 10-fold (e.g., 10-20 fold, 10-50 fold, 10-100 fold, 20-50 fold, 20-100 fold, 30-100 fold, 50-100 fold), optionally at least 50-, 60-, 80- or 100-fold, the minimum concentration required to substantially fully (e.g. 90%, 95%) occupy (saturate) NKG2A receptors on the surface of NKG2A+ cells (e.g., as assessed by titrating anti-NKG2A antibody on NKG2A-expressing cells in PBMC). In one embodiment, the anti-NKG2A antibody competes with HLA-E for binding to human NKG2A.

In one embodiment, provided is a method for treating or preventing a disease (e.g. a cancer, a solid tumor, a hematological tumor) in an individual, the method comprising administering to an individual having disease (e.g. a cancer, a solid tumor) an antibody that neutralizes the inhibitory activity of a human NKG2A polypeptide for at least one administration cycle, the administration cycle comprising at least a first and second (and optionally a $3^{rd}$, $4^{th}$, $5^{th}$, $6^{th}$, $7^{th}$ and/or $8^{th}$ or further) administration of the anti-NKG2A antibody, wherein the anti-NKG2A antibody is administered in an amount effective to achieve, or to maintain between two successive administrations, a blood (serum) concentration of anti-NKG2A antibody of at least 10 µg/ml (or, optionally at least 20, 30, 40 or 50 µg/mL). In one embodiment, a specified continuous blood concentration is maintained, wherein the blood concentration does not drop substantially below the specified blood concentration for the duration of the specified time period (e.g. between two administrations of antibody, number of weeks), i.e. although the blood concentration can vary during the specified time period, the specified blood concentration maintained represents a minimum or "trough" concentration. In one embodiment, a therapeutically active amount of an anti-NKG2A antibody is an amount of such antibody capable of providing (at least) the $EC_{50}$ concentration, optionally substantially the $EC_{100}$ concentration, in blood and/or in a tissue for NKG2A+ NK cell response for a period of at least about 1 week, about 2 weeks, or about one month, following administration of the antibody. In one embodiment, the anti-NKG2A antibody is administered in an amount effective to achieve blood (serum) concentration of anti-NKG2A antibody of at least 10 µg/ml (or, optionally at least 20, 30, 40 or 50 µg/mL) for a period of at least about 1 week, at least about 2 weeks, and that permits a significant "de-saturation" between two successive administrations (successive administrations may for example be separated by one month, two months or more). In one embodiment, a therapeutically active amount of an anti-NKG2A antibody is an amount of such antibody capable of providing (at least) the $EC_{50}$ concentration, optionally substantially the $EC_{100}$ concentration, in a tissue for NKG2A+ NK cell response for a period of at least 1 week, or at least about 2 weeks, following administration of the antibody, and that permits thereafter a significant "de-saturation" between two successive administrations; optionally where the antibody is administered at a dosing frequency of one about every month, or about once every two months. Blood concentration of anti-NKG2A antibody during the desaturation period is below the specified concentration to be achieved during the initial period (e.g. 1 week, 2 weeks, etc.); for example blood and/or tissue concentration of anti-NKG2A antibody during the de-saturation period can be specified to be below the $EC_{100}$, optionally below the $EC_{50}$ for NKG2A+ NK cell response.

In one embodiment, particularly where NKG2A+ T or NK cells in extravascular tissues are intended to be modulated, such as for the treatment of a solid tumor, the anti-NKG2A antibody is administered in an amount effective to achieve a peak concentration, or to maintain a blood concentration, of about or at least about 40, 50, 60, 70 or 80 µg/ml, optionally at least about 100 µg/ml, upon administration (e.g. within 1 or 2 days of administration). In one embodiment, NKG2A antibody is administered in an amount effective to maintain the specified blood concentration for at least one week, optionally at least two weeks, following administration of the anti-NKG2A antibody. In one embodiment, particularly where NKG2A+ T or NK cells in extravascular tissues are intended to be modulated, such as for the treatment of a solid tumor, the anti-NKG2A antibody is administered in an amount effective to achieve, or to maintain, a continuous (minimum) blood concentration of anti-NKG2A antibody of about or at least about 50, 60, 70 or 80 µg/ml, optionally at least about 100 µg/ml, between the first and second (and optionally further) administrations. In one embodiment, successive administrations (e.g. said first and second administrations) are separated in time by at least one week, optionally about two weeks. The anti-NKG2A antibody can optionally be administered in an amount effective and according to a frequency that achieves, or that maintains a blood concentration as specified for the entire duration of the administration cycle.

In one embodiment, provided is a method for treating or preventing a solid tumor in an individual, the method comprising administering to an individual having a solid tumor an antibody that neutralizes the inhibitory activity of a human NKG2A polypeptide for at least one administration cycle, the administration cycle comprising least two administrations of the anti-NKG2A antibody, wherein the anti-NKG2A antibody is administered in an amount effective to achieve, or to maintain, a (minimum) concentration in an extravascular tissue (e.g. in the tumor environment) of at least 4 µg/mL, optionally at least 10 µg/mL between two successive administrations. Optionally, the anti-NKG2A antibody is administered in an amount effective to achieve, or to maintain, a (minimum) concentration in an extravascular tissue (e.g. in the tumor environment) of at least 4 µg/mL, optionally at least 10 µg/mL, for the entire duration of the administration cycle. In one embodiment, the anti-NKG2A antibody is administered in an amount effective to maintain a continuous blood concentration of anti-NKG2A antibody of at least 40 µg/mL, optionally at least 100 µg/mL, between two successive administrations, or for the duration of the administration cycle. In one embodiment, the anti-NKG2A antibody is administered in an amount effective to achieve blood concentration of anti-NKG2A antibody of at least 40 µg/mL, optionally at least 100 µg/mL, upon administration (e.g. for at least one week, at least two weeks upon administration), followed by a period that permits a significant "de-saturation" of NKG2A-expressing cells in circulation between two successive administrations (wherein blood concentration of anti-NKG2A antibody is below said least 40 µg/mL or at least 100 µg/mL during the de-saturation period).

In one embodiment, provided is a method for treating or preventing a hematological tumor in an individual, the method comprising administering to an individual having a hematological tumor an antibody that neutralizes the inhibitory activity of a human NKG2A polypeptide for at least one administration cycle, the administration cycle comprising at least two administrations of the anti-NKG2A antibody, wherein the anti-NKG2A antibody is administered in an amount effective to achieve or maintain a continuous (minimum) blood concentration of anti-NKG2A antibody of at least 10 µg/mL between two successive administrations. Optionally, the anti-NKG2A antibody is administered in an amount effective to achieve or maintain a continuous (minimum) blood concentration of anti-NKG2A antibody of at least 10 µg/mL, for the entire duration of the administration cycle.

In one embodiment, the antibody is administered to achieve a peak blood concentration of at least about 40 µg/mL, optionally about or at least about 100 µg/mL upon administration (e.g. the day of administration, within 24 or 48 hours of administration).

In one embodiment, a blood concentration of 40 µg/ml is capable of providing the $EC_{50}$ concentration for NKG2A+ NK cell response in an extravascular tissue. In one embodiment, a blood concentration of 100 µg/ml is capable of providing the $EC_{100}$ concentration in a tissue (outside of the vasculature, e.g. in the tumor environment) for NKG2A+ NK cell response.

In one embodiment, a method of treatment comprises administering a treatment cycle with (a) an induction (or loading) period wherein a first dosage of anti-NKG2A antibody is administered to achieve or maintain a continuous (minimum) blood concentration of at least about 40 µg/mL, optionally at least about 100 µg/mL, between the first administration and a subsequent administration of anti-NKG2A antibody, (b) a maintenance period, wherein a second, lower, dosage of anti-NKG2A antibody is administered is an amount sufficient to achieve or maintain a continuous (minimum) blood concentration of the anti-NKG2A antibody of at least about 40 µg/mL, optionally at least about 100 µg/mL, until the next administrations of anti-NKG2A antibody (e.g., for the entire treatment cycle). The maintenance period follows the induction period. In one embodiment, the maintenance period comprises at least two administrations of the anti-NKG2A antibody. In one embodiment, the maintenance period comprises at least two administrations at a dose and frequency that provides a continuous blood concentration of the anti-NKG2A antibody of at least about 40 µg/mL, optionally at least about 100 µg/mL, between two administrations.

In any embodiment, blood concentration can be specified to be blood serum concentration.

In one embodiment, the anti-NKG2A antibody substantially fully neutralizes the inhibitory activity of human CD94/NKG2A in the human patient (in vivo), on NKG2A-positive lymphocytes in circulation or in extravascular tissue, for about one week or for about two weeks.

In one embodiment, provided is a method of treating an individual having a cancer (e.g. a solid tumor), the method comprising administering to the individual an antibody that binds and neutralizes the inhibitory activity of NKG2A for at least one administration cycle in which the anti-NKG2A antibody is administered two times per month intravenously at a dose of between 4-10 mg/kg, optionally 4-6 mg/kg, optionally 4-8 mg/kg, optionally about 4 mg/kg, optionally about 6 mg/kg, optionally about 8 mg/kg, or optionally about 10 mg/kg body weight.

In one embodiment, provided is a method of treating an individual having a cancer (e.g. a solid tumor), the method comprising administering to the individual an antibody that binds and neutralizes the inhibitory activity of NKG2A for at least one administration cycle, wherein the method comprises:

a. a loading period in which antibody is administered intravenously at least once at an initial dose of between 8-10 mg/kg, optionally about 10 mg/kg, and, b. a maintenance period in which the antibody is administered intravenously every two weeks at least twice in a dose of between 2-6 mg/kg, optionally between 2-5 mg/kg, optionally between 2-4 mg/kg, optionally about 2 mg/kg, optionally about 3 mg/kg, optionally about 4 mg/kg, or optionally about 6 mg/kg body weight, optionally wherein the first administration within the maintenance period occurs no more than two weeks after the initial dose.

In one embodiment, a therapeutic regimen described herein is administered to an individual having a cancer prior to the individual receiving surgery to remove cancer cells, i.e. the anti-NKG2A antibody regimen is used as a preoperative treatment. In one embodiment, a therapeutic regimen or course of therapy designed to achieve a concentration of anti-NKG2A antibody that corresponds to at least the $EC_{50}$, optionally the $EC_{100}$, for NKG2A+ NK cell response in the extravascular tumor environment is administered to an individual having a cancer prior to surgery to remove cancer cells, i.e. as a preoperative treatment.

In one embodiment, the anti-NKG2A antibody is administered to an individual having cancer cells that express HLA-E at their surface. Optionally, HLA-E status of a cancer can be assessed prior to treatment with an anti-NKG2A antibody. In one embodiment provided is a method combining a HLA-E detection step to identify patients having HLA-E+ tumor; these patients can thereafter be treated with an anti-NKG2A antibody according to the treatment methods described herein.

In one embodiment of any of the therapeutic uses or cancer treatment or prevention methods herein, the treatment or prevention of a cancer in an individual comprises:

a) determining the HLA-E polypeptide status of malignant cells within the individual having a cancer, and b) upon a determination that the patient has HLA-E polypeptides prominently expressed on the surface of malignant cells, administering to the individual an anti-NKG2A antibody that binds and neutralizes the inhibitory activity of NKG2A, e.g. according to any of the treatment methods described herein. Optionally, the antibody interferes with the binding of NKG2A by HLA-E.

In one embodiment of any of the therapeutic uses or cancer treatment or prevention methods herein, the treatment or prevention of a cancer in an individual comprises:

a) determining the level of expression of HLA-E nucleic acid or polypeptides of malignant cells within the individual having a cancer, and b) upon a determination that malignant cells express HLA-E nucleic acid or polypeptide at a level that is increased (e.g. a high value, strong surface staining, etc.) optionally compared to a reference level, administering to the individual an anti-NKG2A antibody that binds and neutralizes the inhibitory activity of NKG2A, e.g. according to any of the treatment methods described herein. Optionally, the antibody interferes with the binding of NKG2A by HLA-E.

In one embodiment of any of the methods, determining the HLA-E polypeptide status or determining the level of expression in step (a) comprises determining the level of expression of a HLA-E nucleic acid or polypeptide of malignant cells in a biological sample and comparing the level to a reference level (e.g. a value, weak cell surface staining, etc.). The reference level may, for example, correspond to a healthy individual, to an individual deriving no/low clinical benefit from treatment with an anti-NKG2A antibody, or to an individual deriving substantial clinical benefit from treatment with an anti-NKG2A antibody. A determination that a biological sample expresses HLA-E nucleic acid or polypeptide at a level that is increased (e.g. a high value, strong surface staining, a level that corresponds to that of an individual deriving substantial clinical benefit from treatment with an anti-NKG2A antibody, a level that is higher than that corresponding to an individual deriving no/low clinical benefit from treatment with an anti-NKG2A antibody, etc.) indicates that the individual has a cancer that can be treated with an anti-NKG2A antibody, e.g. according to the treatment methods described herein.

In one embodiment, the anti-NKG2A antibody is administered as single agent therapy. In one embodiment, the anti-NKG2A antibody is administered in combination treatment with one or more other anti-cancer agents.

In one embodiment of any of the therapeutic uses or treatment or prevention methods herein, the method further comprises administering to an individual a therapeutically active amount of a second anti-cancer agent. In one embodiment, the cancer is a solid tumor. In one embodiment, the second anti-cancer agent is an antibody that is capable of mediating ADCC (e.g. binds, via its Fc domain to human Fcγ receptors, such as CD16. In one embodiment, the antibody that mediates ADCC is administered in an effective amount that elicits antibody-dependent cellular cytotoxicity toward human tumor cells in the human patient (in vivo) that express a polypeptide to which the second anti-cancer agent is directed.

In one embodiment, the second anti-cancer agent is an anti-EGFR antibody. In one embodiment, a patient treated with an anti-NKG2A antibody according to a treatment regimen of the invention, in combination with an anti-EGFR antibody, has an insufficient response to prior treatment with anti-EGFR antibody (e.g. is a non-responder or has progressing disease), or has an unfavorable prognosis for response to treatment with an anti-EGFR antibody (in the absence of treatment with anti-NKG2A).

In one aspect, the combination is administered (or is for administration) according to a particular clinical dosage regimen, notably at a particular dose amount and according to a specific dosing schedule (e.g. a dose amount and/or according to a specific dosing schedule provided herein).

The antibody that neutralizes the inhibitory activity of a NKG2A polypeptide (anti-NKG2A agent) is an antibody that increases the ability of an NKG2A-expressing NK and/or T cells to cause the death of the HLA-E-expressing cell.

In one embodiment, the anti-NKG2A agent reduces the inhibitory activity of NKG2A by blocking binding of its ligand, HLA-E, i.e., the anti-NKG2A agent interferes with the binding of NKG2A by HLA-E. The antibody having the heavy chain of any one of SEQ ID NOS: 2 to 6 and the light chain of SEQ ID NO: 7 respectively, is an example of such an antibody.

In one embodiment, the anti-NKG2A antibody is antibody which binds with a significantly higher affinity to NKG2A than to one or more activating NKG2 receptors. For example, in one embodiment, the antibody binds with a significantly higher affinity to NKG2A than to NKG2C. In an additional or alternative embodiment, the antibody binds with a significantly higher affinity to NKG2A than to NKG2E. In an additional or alternative embodiment, the antibody binds with a significantly higher affinity to NKG2A than to NKG2H. The antibody having a heavy chain of any one of SEQ ID NOS: 2-6 and a light chain of SEQ ID NO: 7, binds NKG2A without substantially binding to NKG2C, NKG2E or NKG2H.

In an additional or alternative embodiment, the anti-NKG2A antibody binds the same epitope on NKG2A and/or competes for binding to CD94/NKG2A with the antibody having a heavy chain of any one of SEQ ID NOS: 2-6 and a light chain of SEQ ID NO: 7. The antibody can be, e.g., a human or humanized anti-NKG2A antibody.

In one embodiment, the anti-NKG2A antibody is a humanized antibody having the heavy chain CDRs of any one of the heavy chain sequences of SEQ ID NOS: 2-6 and the light chain CDRs of the light chain sequence of SEQ ID NO: 7. Exemplary complementarity-determining region (CDR) residues or sequences and/or sites for amino acid substitutions in framework region (FR) of such humanized antibodies having improved properties such as, e.g., lower immunogenicity, improved antigen-binding or other functional properties, and/or improved physicochemical properties such as, e.g., better stability, are provided.

In other embodiments, pharmaceutical compositions and kits are provided, as well as methods for using them.

These aspects are more fully described in, and additional aspects, features, and advantages will be apparent from, the description of the invention provided herein.

BRIEF DESCRIPTION OF THE DRAWINGS

FIG. 4A shows controls and K562 targets with low or high levels of surface HLA-E, and FIG. 4B demonstrates anti-NKG2A can restore lysis of HNSCC with endogenous HLA-E expression. This effect is only seen on NKG2A positive NK cells and is dependent on the level of expression of HLA-E.

FIG. 3A shows CD107 read out on controls with no target and with K562-HLA-E transfectants. Each healthy volunteer is represented by a different symbol: squares or circles. Crossed open symbols correspond to condition where anti-NKG2A was replaced by 10 µg/mL hIgG4 isotypic control co-incubated with 0.1 µg/mL cetuximab. FIG. 6B shows CD107 read out on HNSCC cell lines. For each concentration of cetuximab, the symbols (squares of circles) for each concentration of anti-NKG2A correspond, from left to right, to 0 µg/ml, 0.1 µg/ml, 1 µg/ml, and 10 µg/ml.

DEFINITIONS

Figure 1:
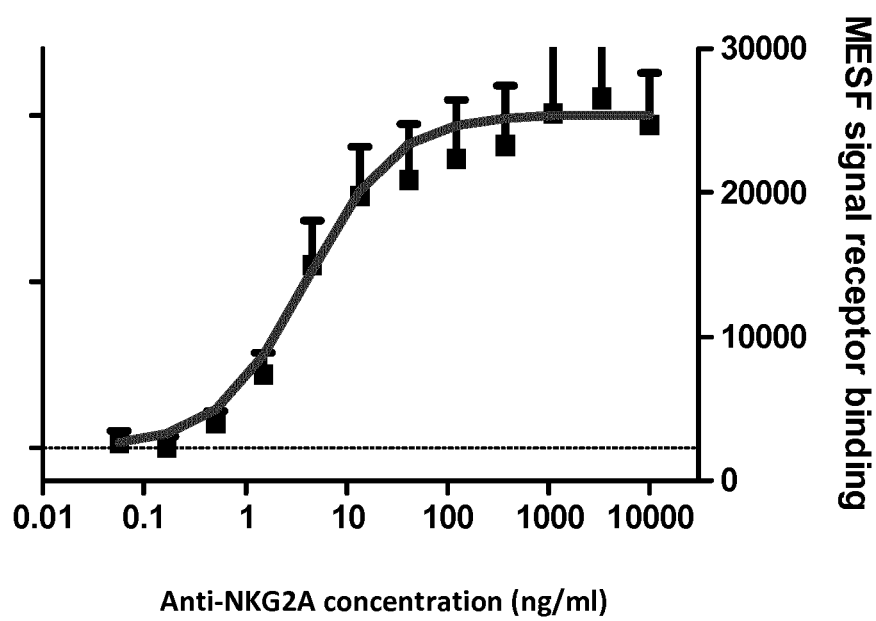
FIG. 1 shows receptor occupancy in human blood of anti-NKG2A antibody (humZ270 also referred to as IPH2201) at different concentrations (ng/ml) listed on the x-axis and MESF signal for receptor binding is shown on the y-axis. The antibody had a binding affinity (EC50) of about 4 ng/mL for NKG2A+ cells ($K_D$~4 ng/mL). This $K_D$ is consistent with $K_D$ values observed in other assays, notably affinity for binding to PBMC and affinity for recombinant NKG2A in Biacore assays. The $K_D$ for full receptor occupancy (the EC100) was about 100 ng/ml.

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. Together with CD94, NKG2A forms the heterodimeric inhibitory receptor CD94/NKG2A, found on the surface of subsets of NK cells, α/β T cells, γ/δ T cells, and NKT cells. Similar to inhibitory KIR receptors, it possesses an ITIM in its cytoplasmic domain. As used herein, "NKG2A" refers to any variant, derivative, or isoform of the NKG2A gene or encoded protein. Also encompassed are any nucleic acid or protein sequences sharing one or more biological properties or functions with wild type, full length NKG2A, and sharing at least 70%, 80%, 90%, 95%, 96%, 97%, 98%, 99%, or higher nucleotide or amino acid identity. Human NKG2A comprises 233 amino acids in 3 domains, with a cytoplasmic domain comprising residues 1-70, a transmembrane region comprising residues 71-93, and an extracellular region comprising residues 94-233, of the following sequence:

(SEQ ID NO: 1)
MDNQGVIYSDLNLPPNPKRQQRKPKGNKSSILATEQEITYAELNLQKA

SQDFQGNDKTYHCKDLPSAPEKLIVGILGIICLILMASVVTIVVIPST

LIQRHNNSSLNTRTQKARHCGHCPEEWITYSNSCYYIGKERRTWEESL

LACTSKNSSLLSIDNEEEMKFLSIISPSSWIGVFRNSSHHPWVTMNGL

AFKHEIKDSDNAELNCAVLQVNRLKSAQCGSSIIYHCKHKL.

NKG2C (OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). The CD94/NKG2C and CD94/NKG2E receptors are activating receptors found on the surface of subsets of lymphocytes such as NK cells and T-cells.

HLA-E (OMIM 143010, the entire disclosure of which is herein incorporated by reference) is a nonclassical MHC molecule that is expressed on the cell surface and regulated by the binding of peptides, e.g., such as fragments derived from the signal sequence of other MHC class I molecules. Soluble versions of HLA-E have also been identified. In addition to its T-cell receptor binding properties, HLA-E binds subsets of natural killer (NK) cells, natural killer T-cells (NKT) and T cells (α/β and γ/δ), by binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E protects target cells from lysis by CD94/NKG2A+ NK, T, or NKT cell clones. As used herein, "HLA-E" refers to any variant, derivative, or isoform of the HLA-E gene or encoded protein. Also encompassed are any nucleic acid or protein sequences sharing one or more biological properties or functions with wild type, full length HLA-E, and sharing at least 70%, 80%, 90%, 95%, 96%, 97%, 98%, 99%, or higher nucleotide or amino acid identity.

In the context of the present invention, "CD94/NKG2A positive lymphocyte" refers to cells of the lymphoid lineage (e.g. NK-, NKT- and T-cells) expressing CD94/NKG2A on the cell-surface, which can be detected by e.g. flow-cytometry using antibodies that specifically recognize a combined epitope on CD94 and NKG2A or and epitope on NKG2A alone. "CD94/NKG2A positive lymphocyte" also includes immortal cell lines of lymphoid origin (e.g. NKL, NK-92).

In the context of the present invention, "reduces the inhibitory activity of NKG2A", "neutralizes NKG2A" or "neutralizes the inhibitory activity of NKG2A" refers to a process in which CD94/NKG2A is inhibited in its capacity to negatively affect intracellular processes leading to lymphocyte responses such as cytokine release and cytotoxic responses. This can be measured for example in a NK- or T-cell based cytotoxicity assay, in which the capacity of a therapeutic compound to stimulate killing of HLA-E positive cells by CD94/NKG2A positive lymphocytes is measured. In one embodiment, an antibody preparation causes at least a 10% augmentation in the cytotoxicity of a CD94/NKG2A-restricted lymphocyte, preferably at least a 40% or 50% augmentation in lymphocyte cytotoxicity, or more preferably at least a 70% augmentation in NK cytotoxicity", and referring to the cytotoxicity assays described. If an anti-NKG2A antibody reduces or blocks CD94/NKG2A interactions with HLA-E, it may increase the cytotoxicity of CD94/NKG2A-restricted lymphocytes. This can be evaluated, for example, in a standard 4-hour in vitro cytotoxicity assay using, e.g., NK cells that express CD94/NKG2A, and target cells that express HLA-E. Such NK cells do not efficiently kill targets that express HLA-E because CD94/NKG2A recognizes HLA-E, leading to initiation and propagation of inhibitory signaling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). Chromium release and/or other parameters to assess the ability of the antibody to stimulate lymphocytes to kill target cells such as P815, K562 cells, or appropriate tumor cells are also disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference. The target cells are labeled with $^{51}$Cr prior to addition of NK cells, and then the killing is estimated as proportional to the release of $^{51}$Cr from the cells to the medium, as a result of killing. The addition of an antibody that prevents CD94/NKG2A from binding to HLA-E results in prevention of the initiation and propagation of inhibitory signaling via CD94/NKG2A. Therefore, addition of such agents results in increases in lymphocyte-mediated killing of the target cells. This step thereby identifies agents that prevent CD94/NKG2A-induced negative signaling by, e.g., blocking ligand binding. In a particular $^{51}$Cr-release cytotoxicity assay, CD94/NKG2A-expressing NK effector-cells can kill HLA-E-negative LCL 721.221 target cells, but less well HLA-E-expressing LCL 721.221-Cw3 control cells. In contrast, YTS effector-cells that lack CD94/NKG2A kill both cell-lines efficiently. Thus, NK effector cells kill less efficiently HLA-E$^+$ LCL 721.221-Cw3 cells due to HLA-E-induced inhibitory signaling via CD94/NKG2A. When NK cells are pre-incubated with blocking anti-CD94/NKG2A antibodies according to the present invention in such a $^{51}$Cr-release cytotoxicity assay, HLA-E-expressing LCL 721.221-Cw3 cells are more efficiently killed, in an antibody-concentration-dependent fashion. The inhibitory activity (i.e. cytotoxicity enhancing potential) of an anti-NKG2A antibody can also be assessed in any of a number of other ways, e.g., by its effect on intracellular free calcium as described, e.g., in Sivori et al., J. Exp. Med. 1997; 186:1129-1136, the disclosure of which is herein incorporated by reference. Activation of NK cell cytotoxicity can be assessed for example by measuring an increase in cytokine production (e.g. IFN-γ production) or cytotoxicity markers (e.g. CD107 or CD137 mobilization). In an exemplary protocol, IFN-y production from PBMC is assessed by cell surface and intracytoplasmic staining and analysis by flow cytometry after 4 days in culture. Briefly, Brefeldin A (Sigma Aldrich) is added at a final concentration of 5 μg/ml for the last 4 hours of culture. The cells are then incubated with anti-CD3 and anti-CD56 mAb prior to permeabilization (IntraPrep™; Beckman Coulter) and staining with PE-anti-IFN-y or PE-IgG1 (Pharmingen). GM-CSF and IFN-y production from polyclonal activated NK cells are measured in supernatants using ELISA (GM-CSF: DuoSet Elisa, R&D Systems, Minneapolis, Minn., IFN-y: OptEIA set, Pharmingen).

Whenever within this whole specification "treatment of cancer" or the like is mentioned with reference to anti-NKG2A binding agent (e.g. antibody), there is meant: (a) method of treatment of cancer, said method comprising the step of administering (for at least one treatment) an anti-NKG2A binding agent, (preferably in a pharmaceutically acceptable carrier material) to an individual, a mammal, especially a human, in need of such treatment, in a dose that allows for the treatment of cancer, (a therapeutically effective amount), preferably in a dose (amount) as specified herein; (b) the use of an anti-NKG2A binding agent for the treatment of cancer, or an anti-NKG2A binding agent, for use in said treatment (especially in a human); (c) the use of an anti-NKG2A binding agent for the manufacture of a pharmaceutical preparation for the treatment of cancer, a method of using an anti-NKG2A binding agent for the manufacture of a pharmaceutical preparation for the treatment of cancer, comprising admixing an anti-NKG2A binding agent with a pharmaceutically acceptable carrier, or a pharmaceutical preparation comprising an effective dose of an anti-NKG2A binding agent that is appropriate for the treatment of cancer; or (d) any combination of a), b), and c), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. NKG2A, as assessed using either recombinant forms of the proteins, epitopes therein, or native proteins present on the surface of isolated target cells. Competitive binding assays and other methods for determining specific binding are well known in the art. For example binding can be detected via radiolabels, physical methods such as mass spectrometry, or direct or indirect fluorescent labels detected using, e.g., cytofluorometric analysis (e.g. FACScan). Binding above the amount seen with a control, non-specific agent indicates that the agent binds to the target. An agent that specifically binds NKG2A may bind NKG2A alone or NKG2A as a dimer with CD94.

When an antibody is said to "compete with" a particular monoclonal antibody, it means that the antibody competes with the monoclonal antibody in a binding assay using either recombinant molecules (e.g., NKG2A) or surface expressed molecules (e.g., NKG2A). For example, if a test antibody reduces the binding of an antibody having a heavy chain of any one of SEQ ID NOS: 2-6 and a light chain of SEQ ID NO: 7 to a NKG2A polypeptide or NKG2A-expressing cell in a binding assay, the antibody is said to "compete" respectively with such antibody.

The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "foot-print" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Production of Antibodies

The anti-NKG2A agent binds an extra-cellular portion of human CD94/NKG2A receptor and reduces the inhibitory activity of human CD94/NKG2A receptor expressed on the surface of a CD94/NKG2A positive lymphocyte. In one embodiment the agent competes with HLA-E in binding to CD94/NKG2A, i.e. the agent interferes with and reduces the interaction between CD94/NKG2A and its ligand HLA-E. The antibody may bind a combined epitope on CD94 and NKG2A or an epitope on NKG2A alone. In one embodiment, the antibody binds an epitope on NKG2A which at least partly overlaps with the HLA-E binding site.

In one aspect the anti-NKG2A agent is an antibody selected from a fully human antibody, a humanized antibody, and a chimeric antibody. In one aspect, the agent comprises a constant domain derived from a human IgG1, IgG2, IgG3 or IgG4 antibody. In one aspect, the agent is a fragment of an antibody selected from IgA, an IgD, an IgG, an IgE and an IgM antibody. In one aspect, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect, the agent is a synthetic or semisynthetic antibody-derived molecule selected from a scFV, a dsFV, a minibody, a diabody, a triabody, a kappa body, an IgNAR; and a multispecific antibody.

Preferably, the anti-NKG2A antibodies do not demonstrate substantial specific binding to Fcγ receptors, e.g. CD16. Such antibodies may comprise constant regions of various heavy chains that are known not to bind Fc receptors. One such example is a human IgG4 constant region. In one embodiment, the IgG4 antibody comprises a modification to prevent the formation of half antibodies (fab arm exchange) in vivo, e.g., the antibody comprises an IgG4 heavy chain comprising a serine to proline mutation in residue 241, corresponding to position 228 according to the EU-index (Kabat et al., "Sequences of proteins of immunological interest", $5^{th}$ ed., NIH, Bethesda, ML, 1991). Such modified IgG4 antibodies will remain intact in vivo and maintain a bivalent (high affinity) binding to NKG2A, as opposed to native IgG4 that will undergo fab arm exchange in vivo such that they bind to NKG2A in monovalent manner which can alter binding affinity. Alternatively, antibody fragments that do not comprise one or more constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any human antibody type (e.g. IgG1, IgG2, IgG3 or IgG4) can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

An anti-NKG2A antibody can advantageously bind to an extracellular portion of NKG2A with a KD that is at least 100 fold lower than the KD for binding to NKG2C. In a one aspect, the antibody binds to an extracellular portion of NKG2A with a KD that is at least 150, 200, 300, 400, or 10,000 fold lower than the KD for binding to NKG2C. In another aspect, the antibody binds to an extracellular portion of NKG2A with a KD that is at least 100 fold lower than the KD for binding to NKG2C, NKG2E and/or NKG2H molecules. In a further aspect, the antibody binds to an extracellular portion of NKG2A with a KD that is at least 150, 200, 300, 400, or 10,000 fold lower than the KD for binding to NKG2C, NKG2C and/or NKG2H molecules. This can be measured, for instance, in BiaCore experiments, in which the capacity of agents to bind the extracellular portion of immobilized CD94/NKG2A (e.g. purified from CD94/NKG2 expressing cells, or produced in a bio-system) is measured and compared to the binding of agents to similarly produced CD94/NKG2C and/or other CD94/NKG2 variants in the same assay. Alternatively, the binding of antibodies to cells that either naturally express, or over-express (e.g. after transient or stable transfection), CD94/NKG2A can be measured and compared to binding of cells expressing CD94/NKG2C and/or other CD94/NKG2 variants. Anti-NKG2A antibodies may optionally bind NKG2B, which is an NKG2A splice variant forming an inhibitory receptor together with CD94. In one embodiment, affinity can be measured using the methods disclosed in U.S. Pat. No. 8,206,709, for example by assessing binding to covalently immobilized NKG2A-CD94-Fc fusion protein by Biacore as shown in Example 8 of U.S. Pat. No. 8,206,709, the disclosure of which is incorporate herein by reference.

The antibody can for example have an $EC_{50}$ for binding (high affinity) to NKG2A-expressing cells of between 0.5-10 ng/ml, optionally 1-5 ng/ml, optionally 1-10 ng/ml, optionally 1-20 ng/ml, e.g. about 4 ng/ml. The NKG2A-expressing cells can be, for example, NKG2A-expressing cells in human PBMC. In one embodiment, the NKG2A-expressing cells are cells made to express CD94/NKG2A, for example Ba/F3 cells stably overexpressing CD94/NKG2A as shown in Example 13 of U.S. Pat. No. 8,206,709, the disclosure of which is incorporated by reference. In one embodiment, the antibody has binding affinity ($K_D$), optionally wherein binding affinity is bivalent, for a human NKG2A polypeptide of less than $10^{-9}$ M, optionally less than $10^{-10}$ M, or optionally less than $10^{-11}$ M, optionally between than $10^{-10}$ M and $10^{-12}$ M, optionally between than $10^{-10}$ M and $10^{-11}$ M. Affinity can be assessed, for example, for binding to a single-chain NKG2A-CD94-mFc construct as described in U.S. Pat. No. 7,932,055, the disclosure of which is incorporated by reference).

The anti-NKG2A antibody can be a human or humanized antibody, for example comprising a VH human acceptor framework from a human acceptor sequence selected from, e.g., VH1_18, VH5_a, VH5_51, VH1_f, and VH1_46, and a JH6 J-segment, or other human germline VH framework sequences known in the art. The VL region human acceptor sequence may be, e.g., VKI_O2/JK4.

In one embodiment, the antibody is a humanized antibody based on antibody Z270. Different humanized Z270VH chains are shown in SEQ ID NOS: 2-6 (variable region domain amino acids underlined). Humanized Z270VH light chain is shown in SEQ ID NO: 7. HumZ270 antibody is also disclosed in U.S. Pat. No. 8,206,709 (the disclosure of which is incorporated herein by reference). HumZ270VH6 (SEQ ID NO: 2) is based on VH5_51; HumZ270VH1 (SEQ ID NO: 3) is based on VH1_18; humZ270VH5 (SEQ ID NO: 4) is based on VH5_a; humZ270VH7 (SEQ ID NO: 5) is based on VH1_f; and humZ270VH8 (SEQ ID NO: 6) is based on VH1_46; all with a JH6 J-segment. Each of these antibodies retains high affinity binding to NKG2A, with low likelihood of a host immune response against the antibody as the 6 C-terminal amino acid residues of the Kabat CDR-H2 of each of the humanized constructs are identical to the human acceptor framework. Using the alignment program VectorNTI, the following sequence identities between humZ270VH1 and humZ270VH5, -6, -7, and -8 were obtained: 78.2% (VH1 vs. VH5), 79.0% (VH1 vs. VH6), 88.7% (VH1 vs. VH7), and 96.0% (VH1 vs. VH8).

In one aspect, the agent comprises (i) a heavy chain variable region of any of SEQ ID NOS: 2-6, or an amino acid sequence at least 50%, 60%, 70%, 80%, 90%, 95%, 98% or 99% identical thereto, and (ii) a light chain variable region of SEQ ID NO: 7, or an amino acid sequence at least 50%, 60%, 70%, 80%, 90%, 95%, 98% or 99% identical thereto. In one aspect, the agent comprises (i) a heavy chain comprising the amino acid sequence of any of SEQ ID NOS: 2-6, or an amino acid sequence at least 50%, 60%, 70%, 80%, 90%, 95%, 98% or 99% identical thereto, and (ii) a light chain comprising the amino acid sequence of SEQ ID NO: 7, or an amino acid sequence at least 50%, 60%, 70%, 80%, 90%, 95%, 98% or 99% identical thereto. The antibody having the heavy chain comprising the sequence of any of SEQ ID NOS: 2-6 and a light chain comprising the sequence of SEQ ID NO: 7 neutralizes the inhibitory activity of NKG2A, but does not substantially bind the activating receptors NKG2C, NKGE or NKG2H. This antibody furthermore competes with HLA-E for binding to NKG2A on the surface of a cell. In one aspect, the agent comprises HCDR1, HCDR2 and/or HCDR3 sequences derived from the heavy chain having the amino acid sequence of any of SEQ ID NO: 2-6. In one aspect of the invention, the agent comprises LCDR1, LCDR2 and/or LCDR3 sequences derived from the light chain having the amino acid sequence of SEQ ID NO: 7.

```
Heavy Chains (variable regions underlined)
VH6:
                                          (SEQ ID NO: 2)
EVQLVQSGAEVKKPGESLKISCKGSGYSFTSYWMNWVRQMPGKGLEWM

GRIDPYDSETHYSPSFQGQVTISADKSISTAYLQWSSLKASDTAMYYC

ARGGYDFDVGTLYWFFDVWGQGTTVTVSSASTKGPSVFPLAPCSRSTS

ESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSV

MHEALHNHYTQKSLSLSLGK

VH1:
                                          (SEQ ID NO: 3)
QVQLVQSGAEVKKPGASVKVSCKASGYTFTSYWMNWVRQAPGQGLEWM

GRIDPYDSETHYAQKLQGRVTMTTDTSTSTAYMELRSLRSDDTAVYYC

ARGGYDFDVGTLYWFFDVWGQGTTVTVSSASTKGPSVFPLAPCSRSTS

ESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVE
```

-continued
VHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSV

MHEALHNHYTQKSLSLSLGK

VH5:
(SEQ ID NO: 4)
EVQLVQSGAEVKKPGESLRISCKGSGYSFTSYWMNWVRQMPGKGLEWM

GRIDPYDSETHYSPSFQGHVTISADKSISTAYLQWSSLKASDTAMYYC

ARGGYDFDVGTLYWFFDVWGQGTTVTVSSASTKGPSVFPLAPCSRSTS

ESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSV

MHEALHNHYTQKSLSLSLGK

VH7:
(SEQ ID NO: 5)
EVQLVQSGAEVKKPGATVKISCKVSGYTFTSYWMNWVQQAPGKGLEWM

GRIDPYDSETHYAEKFQGRVTITADTSTDTAYMELSSLRSEDTAVYYC

ATGGYDFDVGTLYWFFDVWGQGTTVTVSSASTKGPSVFPLAPCSRSTS

ESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSV

MHEALHNHYTQKSLSLSLGK

VH8:
(SEQ ID NO: 6)
QVQLVQSGAEVKKPGASVKVSCKASGYTFTSYWMNWVRQAPGQGLEWM

GRIDPYDSETHYAQKFQGRVTMTRDTSTSTVYMELSSLRSEDTAVYYC

ARGGYDFDVGTLYWFFDVWGQGTTVTVSSASTKGPSVFPLAPCSRSTS

ESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSV

MHEALHNHYTQKSLSLSLGK

Light chain
(SEQ ID NO: 7)
DIQMTQSPSSLSASVGDRVTITCRASENIYSYLAWYQQKPGKAPKLLI

YNAKTLAEGVPSRFSGSGSGTDFTLTISSLQPEDFATYYCQHHYGTPR

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

In one aspect, the anti-NKG2A antibody is an antibody comprising a CDR-H1 corresponding to residues 31-35 of any of SEQ ID NOS: 2-6 (the amino acid sequence SYWMN (SEQ ID NO: 8)), a CDR-H2 corresponding to residues 50-60 (the amino acid sequence RIDPYDSETHY (SEQ ID NO: 9)) (optionally 50-66 when including the 6 terminal amino acids of human origin, i.e. the sequence RIDPYDSETHYSPSFQG (SEQ ID NO: 10) for the VH6 heavy chain, the sequence RIDPYDSETHYAQKLQG (SEQ ID NO: 11) for the VH1 heavy chain, etc.) of any of SEQ ID NOS: 2-6, and a CDR-H3 corresponding to residues 99-114 (95-102 according to Kabat) of any of SEQ ID NOS: 2-6 (the amino acid sequence GGYDFDVGTLYWFFDV (SEQ ID NO: 12)). In one embodiment, the CDR-H2 corresponding to residues 50-66 of any of SEQ ID NOS: 2-6. Optionally, a CDR may comprise one, two, three, four, or more amino acid substitutions.

In one aspect, the anti-NKG2A antibody is an antibody comprising a CDR-L1 corresponding to residues 24-34 of SEQ ID NO: 7 (the amino acid sequence RASENIYSYLA (SEQ ID NO: 13)), a CDR-L2 corresponding to residues 50-56 of SEQ ID NO: 7 (the amino acid sequence NAKTLAE (SEQ ID NO: 14)), and an CDR-L3 corresponding to residues 89-97 of SEQ ID NO: 7 (the amino acid sequence QHHYGTPRT (SEQ ID NO: 15)). Optionally, a CDR may comprise one, two, three, four, or more amino acid substitutions.

In one aspect, the anti-NKG2A antibody is an antibody comprising a CDR-H1 corresponding to residues 31-35 of any of SEQ ID NOS: 2-6, a CDR-H2 corresponding to residues 50-60 (optionally 50-66) of any of SEQ ID NOS: 2-6, and a CDR-H3 corresponding to residues 99-114 (95-102 according to Kabat) of any of SEQ ID NOS: 2-6, a CDR-L1 corresponding to residues 24-34 of SEQ ID NO: 7, a CDR-L2 corresponding to residues 50-56 of SEQ ID NO: 7, and an CDR-L3 corresponding to residues 89-97 of SEQ ID NO: 7.

In one aspect, the agent is a fully human antibody which has been raised against the CD94/NKG2A epitope to which any of the aforementioned antibodies bind.

It will be appreciated that, while the aforementioned antibodies can be used, other antibodies can be prepared. For example, any fragment of NKG2A, preferably but not exclusively human NKG2A, or any combination of NKG2A fragments, can be used as immunogens to raise antibodies, and the antibodies can recognize epitopes at any location within the NKG2A polypeptide, so long as they can do so on NKG2A expressing NK cells as described herein. Most preferably, the epitope is the epitope specifically recognized by antibody having the heavy chain of any of SEQ ID NOS: 2-6 and the light chain of SEQ ID NO: 7.

In one aspect, the agent competes with humZ270 antibody disclosed in U.S. Pat. No. 8,206,709 (the disclosure of which is incorporated herein by reference) in binding to the extracellular portion of human CD94/NKG2A receptor. Competitive binding can be measured, for instance, in BiaCore experiments, in which the capacity of agents is measured, for binding the extracellular portion of immobilized CD94/NKG2A receptor (e.g. purified from CD94/NKG2 expressing cells, or produced in a bio-system) saturated with humZ270. Alternatively, the binding of agents to cells is measured that either naturally express, or over-express (e.g.

after transient or stable transfection), CD94/NKG2A receptor, and which have been pre-incubated with saturating doses of Z270. In one embodiment, competitive binding can be measured using the methods disclosed in U.S. Pat. No. 8,206,709, for example by assessing binding to Ba/F3-CD94-NKG2A cells by flow cytometry as shown in Example 15 of U.S. Pat. No. 8,206,709, the disclosure of which is incorporate herein by reference.

An anti-NKG2A antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation further comprises a pharmaceutically acceptable preservative. In a further embodiment, the formulation further comprises an isotonic agent. In a further embodiment, the formulation also comprises a chelating agent. In a further embodiment of the invention the formulation further comprises a stabilizer. In a further embodiment, the formulation further comprises a surfactant. For convenience reference is made to Remington: *The Science and Practice of Pharmacy*, 19$^{th}$ edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an antibody may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Diagnosis and Treatment of Malignancies

Described are methods useful in the diagnosis, prognosis, monitoring, treatment and prevention of a cancer in an individual. While the methods described herein are particularly useful for the treatment of solid tumors, the treatment regimens described herein can also be used for a variety of hematological cancers, as well as infectious disease, and inflammation and autoimmune disorders. The methods and compositions of the present invention are utilized for example the treatment of a variety of cancers and other proliferative diseases including, but not limited to: carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma, and multiple myeloma; hematopoietic tumors of myeloid lineage, including acute and chronic myelogenous leukemias, promyelocytic leukemia, and myelodysplastic syndrome; tumors of mesenchymal origin, including fibrosarcoma and rhabdomyoscarcoma; other tumors, including melanoma, seminoma, terato-carcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

Examples of hematopoietic tumors of lymphoid lineage, include for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); adult T-cell leukemia lymphoma (ATLL); T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; lym-phoma/leukaemia (T-Lbly/T-ALL), multiple myeloma.

In one embodiment, the cancer is a head and neck squamous cell carcinoma (HNSCC). In one embodiment the HNSCC is an oropharangeal tumor, a larynx tumor, a tumor of the oral cavity, or a tumor of the hypopharynx. In one embodiment, the HNSCC is an oral cavity SCC (OCSCC). OCSCC comprises squamous cell carcinoma of the lip, anterior ⅔ of the tongue, floor of the mouth, buccal mucosa, gingiva, hard palate and retromolar trigone. In one embodiment the HNSCC is a metastatic cancer.

When treating an individual having a solid tumor, a compound (e.g. antibody) that neutralizes the inhibitory activity of a human NKG2A polypeptide can advantageously be administered according to a treatment regimen described herein, to an individual having a cancer who has not received surgery to remove cancer cells, or who has not in the current period received such surgery. However it will be appreciated that the compound can also be administered to a patient who has received, or who is undergoing, surgery to remove cancer cells. Where the anti-NKG2A compound is administered to an individual who has not received surgical intervention to remove cancer cells (e.g. to remove HNSCC cells), the NKG2A-binding compound can for example be administered approximately 1 to 8 weeks prior to surgery. In one embodiment, at least one (e.g. one, two, three or more) complete administration cycle(s) of treatment with anti-NKG2A compound is administered prior to surgery. In one embodiment, the administration cycle is between 2 weeks and 8 weeks.

In one embodiment, the cancer treated with the methods disclosed herein is an HLA-E-expressing cancer.

A patient having a cancer can be treated with the anti-NKG2A agents with or without a prior detection step to assess expression of HLA-E on the surface of tumor cells. Advantageously, the treatment methods can comprises a step of detecting a HLA-E nucleic acid or polypeptide in a biological sample of a tumor (e.g. on a tumor cell) from an individual. Example of biological samples include any suitable biological fluid (for example serum, lymph, blood), cell sample, or tissue sample. For example, a tissue sample may be a sample of tumor tissue or tumor-adjacent tissue. Optionally, HLA-E polypeptide is detected on the surface of a malignant cell. A determination that a biological sample expresses HLA-E (e.g. prominently expresses; expresses HLA-E at a high level, high intensity of staining with an anti-HLA-E antibody, compared to a reference) indicates that the individual has a cancer that may have a strong benefit from treatment with an agent that inhibits NKG2A. In one embodiment, the method comprises determining the level of expression of a HLA-E nucleic acid or polypeptide in a biological sample and comparing the level to a reference level (e.g. a value, weak cell surface staining, etc.) corresponding to a healthy individual. A determination that a biological sample expresses an HLA-E nucleic acid or polypeptide at a level that is increased compared to the reference level indicates that the individual has a cancer that can be treated with an agent that inhibits NKG2A.

In one embodiment, a determination that a biological sample (e.g., a sample comprising tumor cells, tumor tissue and/or tumor adjacent tissue) prominently expresses HLA-E nucleic acid or polypeptide indicates that the individual has a cancer that can be treated with an agent that inhibits NKG2A. "Prominently expressed", when referring to a HLA-E polypeptide, means that the HLA-E polypeptide is expressed in a substantial number of tumor cells taken from a given individual. While the definition of the term "prominently expressed" is not bound by a precise percentage value, in some examples a receptor said to be "prominently expressed" will be present on at least 30%, 40%, 50%, 60%, 70%, 80%, or more of the tumor cells taken from a patient.

Determining whether an individual has cancer cells that express an HLA-E polypeptide can for example comprise obtaining a biological sample (e.g. by performing a biopsy) from the individual that comprises cancer cells, bringing said cells into contact with an antibody that binds an HLA-E polypeptide, and detecting whether the cells express HLA-E on their surface. Optionally, determining whether an individual has cancer cells that express HLA-E comprises conducting an immunohistochemistry assay. Optionally determining whether an individual has cancer cells that express HLA-E comprises conducting a flow cytometry assay.

In one exemplary aspect, provided is method of reducing progression of cancer in a mammalian host, (e.g., a human patient) having a detectable level of cancer cells comprising administering an anti-NKG2A antibody in a dosage and frequency according to the disclosure sufficient to detectably reduce the progression of the cancer in the host.

In one embodiment, provided is a method for treating or preventing a disease (e.g. a hematological tumor, an inflammatory or autoimmune disease, an infection) in an individual, the method comprising administering to an individual having disease an antibody that neutralizes the inhibitory activity of a human NKG2A polypeptide in an amount that achieves a concentration in circulation that is at least 10, 20, 30 or 50 times higher than the concentration required for substantially full (e.g., 90%, 95%) receptor saturation (e.g., as assessed by titrating anti-NKG2A antibody on NKG2A-expressing cells, for example in PBMC). The antibody can for example have an $EC_{50}$ for binding to NKG2A-expressing cells in human PBMC of between 0.5-10 ng/ml, optionally 1-10 ng/ml, optionally 1-20 ng/ml, e.g. about 4 ng/ml.

In one embodiment, provided is a method for treating or preventing a disease (e.g. a solid tumor, an inflammatory or autoimmune disease, an invention) in an individual, the method comprising administering to an individual having disease an antibody that neutralizes the inhibitory activity of a human NKG2A polypeptide in an amount that achieves a concentration in an extravascular tissue of interest (e.g. the tumor or tumor environment) that is at least 10, 20, 30 or 50 times higher than the concentration required for substantially full (e.g., 90%, 95%) receptor saturation (e.g., as assessed by titrating anti-NKG2A antibody on NKG2A-expressing cells, for example in PBMC).

The $EC_{50}$ for NKG2A+ NK cell response of the blocking anti-NKG2A antibody HumZ270 is about 4 µg/ml, thus an amount of this anti-NKG2A antibody is administered so at to achieve and/or maintain a blood concentration of at least 4 µg/ml. Advantageously an amount of anti-NKG2A antibody is administered to an individual so at to achieve and/or maintain a blood concentration in the individual of at least 10 µg/ml (the $EC_{100}$ for NKG2A+ NK cell response. For example, the blood concentration to be achieved and/or maintained can be between 10-12 µg/ml, 10-15 µg/ml, 10-20 µg/ml, 10-30 µg/ml, 10-40 µg/ml, 10-50 µg/ml, 10-70 µg/ml, 10-100 µg/ml, 10-150 µg/ml or 10-200 µg/ml. In one embodiment, an amount of anti-NKG2A antibody is administered to an individual so at to achieve and/or maintain a tissue concentration in the individual of at least about 4 µg/ml (the $EC_{50}$ for NKG2A+ NK cell response)or optionally at least about 10 µg/ml (the $EC_{100}$ for NKG2A+ NK cell response). When tissues outside of the vasculature are targeted (e.g. in the treatment of solid tumors), an amount of anti-NKG2A antibody is administered so at to achieve and/or maintain a tissue concentration of at least 10 µg/ml; for example, administering an amount of anti-NKG2A antibody to achieve a blood concentration of at least 100 µg/ml is expected to achieve an extravascular tissue (e.g. tumor tissue) concentration of at least 10 µg/ml. For example, the blood concentration to be achieved and/or maintained in order to achieve/maintain 10 µg/ml in a tissue can be between 100-110 µg/ml, 100-120 µg/ml, 100-130 µg/ml, 100-140 µg/ml, 100-150 µg/ml, 100-200 µg/ml, 100-250 µg/ml or 100-300 µg/ml.

In some embodiments, an amount of anti-NKG2A antibody is administered so as to obtain a concentration in blood (serum) that corresponds to at least the $EC_{50}$ for NKG2A+ NK cell response, optionally at about or at least about, the $EC_{100}$. NKG2A+ NK cell response can be assessed using a suitable assay of cytotoxic activity of NKG2A-expressing NK cells toward HLA-E expressing target cells. Examples include assays based on markers of NK cell activation, for example CD107 or CD137 expression as shown in the Examples herein. "$EC_{50}$" with respect to NKG2A+ NK cell response, refers to the efficient concentration of anti-NKG2A antibody which produces 50% of its maximum response or effect with respect to such NKG2A+ NK cell response. "$EC_{100}$" with respect to NKG2A+ NK cell response, refers to the efficient concentration of anti-NKG2A antibody which produces its substantially maximum response or effect with respect to such NKG2A+ NK cell response. In some embodiments, particularly for the treatment of solid tumors, the concentration achieved is designed to lead to a concentration in tissues (outside of the vasculature, e.g. in the tumor or tumor environment) that corresponds to at least the $EC_{50}$ for NKG2A+ NK cell response, optionally at about, or at least about, the $EC_{100}$.

Suitable treatment protocols for treating a human include, for example, administering to the patient an effective amount of an anti-NKG2A antibody, wherein the method comprises at least one administration cycle in which at least one dose of the anti-NKG2A antibody is administered at a dose of 2-10 mg/kg, optionally 4-10 mg/kg, optionally 6-10 mg/kg, optionally 8-10 mg/kg, optionally 2-4 mg/kg, optionally 4-6 mg/kg, optionally 4-8 mg/kg, optionally 6-8 mg/kg body weight. Optionally, at least 2, 3, 4, 5, 6, 7 or 8 doses of the anti-NKG2A antibody are administered. In one embodiment, the administration cycle is between 2 weeks and 8 weeks. In one embodiment, the administration cycle is 8 weeks. In one embodiment, the administration cycle is 8 weeks and comprises administering one dose of the anti-NKG2A antibody every two weeks (i.e. a total of four doses).

In one aspect of any of the embodiments herein, the anti-NKG2A antibody is administered once about every two weeks.

Suitable treatment protocols for treating a human include, for example, administering to the patient an effective amount of an anti-NKG2A antibody, wherein the antibody is administered 2 times per month and the amount effective to maintain a continuous blood concentration of anti-NKG2A antibody of at least 10 µg/ml between at least two successive administrations of the anti-NKG2A antibody is between 2-10 mg/kg, optionally 2-6 mg/kg, optionally 2-8 mg/kg, optionally 2-4 mg/kg, optionally 2-3 mg/kg, or optionally about 2, 3 or 4 mg/kg body weight. These doses can optionally be selected so as to provide for a continued blood concentration of anti-NKG2A antibody of at least 10 µg/ml throughout the treatment cycle. Achieving blood concentration of anti-NKG2A antibody of 10 µg/ml corresponds to the $EC_{100}$ for an antibody such as humanized Z270.

Further suitable treatment protocols for treating a human include, for example, administering to the patient an effective amount of an anti-NKG2A antibody, wherein the antibody is administered two times per month and the amount effective to maintain a continuous blood concentration of anti-NKG2A antibody of at least 40 µg/ml between at least two successive administrations of the anti-NKG2A antibody is between 2-10 mg/kg, optionally 2-8 mg/kg, optionally 2-6 mg/kg, optionally 2-4 mg/kg, optionally 2-3 mg/kg, or optionally about 2, 3 or 4 mg/kg body weight. These doses can optionally be administered so as to provide for continued blood concentration of anti-NKG2A antibody of at least 40 µg/ml throughout the treatment cycle. Achieving blood concentration of anti-NKG2A antibody of 40 µg/ml is expected to provide a tissue (e.g., extravascular tissue, tumor environment of a solid tumor) concentration of about 4 µg/ml, in turn corresponding to the $EC_{50}$ for NKG2A+ NK cell response for an antibody such as humanized Z270.

Further advantageous suitable treatment protocols for treating a human include, for example, administering to the patient an effective amount of an anti-NKG2A antibody, wherein the antibody is administered 2 times per month and the amount effective to maintain a continuous blood concentration of anti-NKG2A antibody of at least 100 µg/ml between at least two successive administrations of the anti-NKG2A antibody is between 4-10 mg/kg, optionally 4-6 mg/kg, optionally 4-8 mg/kg, optionally about 4 mg/kg, optionally about 6 mg/kg, optionally about 8 mg/kg, or optionally about 10 mg/kg body weight. These doses can optionally be administered so as to provide for continued blood concentration of anti-NKG2A antibody of at least 100 µg/ml throughout the treatment cycle. Achieving blood concentration of anti-NKG2A antibody of 100 µg/ml is expected to provide a tissue (e.g., extravascular, tumor environment) concentration of about 10 µg/ml, in turn corresponding to the $EC_{100}$ for an antibody such as humanized Z270.

Further advantageous suitable treatment protocols for treating a human having cancer include regimens that employ a loading period with a higher dose, followed by a maintenance period. For example, a loading period may comprise administering to the patient an effective amount of an anti-NKG2A antibody, wherein the antibody is administered one or more times in an amount effective to maintain a continuous blood concentration of anti-NKG2A antibody of at least 100 µg/ml until the first administration of anti-NKG2A antibody in the maintenance regimen. For example, when administered once, a loading dose of 10 mg/kg of anti-NKG2A antibody can be administered, wherein the first administration of anti-NKG2A antibody within the maintenance regimen occurs about two weeks (or less) after the loading dose. The maintenance regimen can then employ a lower dose and/or lower frequency of administration in order to maintain a continuous blood concentration of anti-NKG2A antibody of at least 100 µg/ml between successive administrations within the maintenance regimen. For example, a maintenance regimen can comprise administering anti-NKG2A antibody every two weeks at a dose of between 2-10 mg/kg, optionally 4-10 mg/kg, optionally 2-4 mg/kg, optionally 4-6 mg/kg, optionally 4-8 mg/kg, optionally about 4 mg/kg, optionally about 6 mg/kg, optionally about 8 mg/kg body weight.

In one aspect, anti-NKG2A antibody is dosed in an amount so as to obtain a concentration in blood (serum) and/or tissue (e.g. tumor tissue) that corresponds to at least the $EC_{50}$ for NKG2A+ NK cell response, optionally at about or at least about, the $EC_{100}$, for a period of at least about 1 week, at least about 2 weeks, without a significant "de-saturation" of NKG2A on cells in circulation between at least two successive administrations of the anti-NKG2A antibody. In another aspect, antibody is dosed in an amount so as to obtain a concentration in blood (serum) and/or tissue (e.g. tumor tissue) that corresponds to at least the $EC_{50}$ for NKG2A+ NK cell response, optionally at about or at least about, the $EC_{100}$, for a period of at least about 1 week, at least about 2 weeks, and that permits a significant "de-saturation" of NKG2A on cells in circulation between two (or between each) successive administrations of the anti-NKG2A antibody. For example, the anti-NKG2A antibody may be administered in an amount and at a frequency may result in at least 50% de-saturation of NKG2A on cells in circulation during the treatment period, for example between two successive administrations of the anti-NKG2A antibody. In one example, the amount that permits a significant "de-saturation" of NKG2A on cells in circulation is an amount that provides a blood concentration of less than the $EC_{50}$ for NKG2A+ NK cell response, optionally less than the $EC_{20}$ for NKG2A+ NK cell response.

Advantageous suitable treatment protocols for treating a human include, for example, administering to the patient an effective amount of an anti-NKG2A antibody, wherein the antibody is administered in an amount effective to achieve a blood concentration of anti-NKG2A antibody of at least 10 μg/ml, 40 μg/ml or 100 μg/ml for a period of at least about 1 week, or at least about 2 weeks, and that permits (e.g. is followed by) a significant "de-saturation" of NKG2A on cells in circulation between two (or between each) successive administrations of the anti-NKG2A antibody.

For example, wherein the antibody is administered no more than once per month (or no more than once about every two months) and the amount effective to achieve a blood concentration of anti-NKG2A antibody of at least 10 μg/ml, 40 μg/ml or 100 μg/ml for a period of at least about 1 week, or at least about 2 weeks is between 2-10 mg/kg, optionally 2-8 mg/kg, optionally 2-6 mg/kg, optionally 2-4 mg/kg, optionally 2-3 mg/kg, or optionally about 2, 3 or 4 mg/kg body weight.

Saturation (and de-saturation) of NKG2A on cells in circulation can be assessed by obtaining a peripheral blood sample and using standard methods for assessing receptor occupancy.

In another aspect, provided is a method of reducing the risk of cancer progression, reducing the risk of further cancer progression in a cell population that has undergone initiation, and/or providing a therapeutic regimen for reducing cancer progression in a human patient, which comprises administering to the patient one or more first treatments (e.g. induction therapy, such as a chemotherapeutic agent) in an amount and regimen sufficient to achieve a response (partial or complete response), and then administering to the patient an amount of an anti-NKG2A antibody in a dosage and frequency according to the disclosure.

In a further aspect, provided is a method of promoting remission of a cancer in an individual, such as a human patient, comprising administering a composition comprising an anti-NKG2A antibody, to the individual, in a dosage and frequency according to the disclosure, so as to promote cancer remission in the individual. In a further aspect, provided is a method of preventing recurrence of a cancer in an individual, such as a human patient, whose cancer is in remission following a preceding anti-cancer treatment, comprising administering to the individual a composition comprising an anti-NKG2A antibody, in a dosage and frequency according to the disclosure, so as to promote cancer remission in the individual.

In an even further aspect, provided is a method for reducing the risk of developing a cancer, reducing the time to onset of a cancerous condition, and/or reducing the severity of a cancer diagnosed in the early stages, comprising administering to an individual a prophylactically effective amount of an anti-NKG2A antibody in a dosage and frequency according to the disclosure, so as to achieve the desired physiological effect(s).

In a further aspect, provided is a method of increasing the likelihood of survival over a relevant period in a human patient diagnosed with cancer. In another aspect, provided is a method for improving the quality of life of a cancer patient comprising administering to the patient a composition in an amount effective to improve the quality of life thereof. In a further aspect, methods described herein can be applied to significantly reduce the number of cancer cells in a vertebrate host, such that, for example, the total number of cancer cells is reduced. In a related sense, provided is a method for killing (e.g. either directly or indirectly causing death of) cancer cells in a vertebrate, such as a human cancer patient.

The anti-NKG2A antibody can be administered as monotherapy or in adjunctive or combined administration (co-administration) with a second therapeutic agent, e.g. an anti-EGFR antibody. The adjunctive or combined administration includes simultaneous administration of the compounds in the same or different dosage form, or separate administration of the compounds (e.g., sequential administration). Thus, the anti-NKG2A and second therapeutic agent can be simultaneously administered in a single formulation. Alternatively, the anti-NKG2A and second therapeutic agent can be formulated for separate administration and are administered concurrently or sequentially. The second therapeutic agent will normally be administered in amounts and treatment regimens typically used for that agent in a monotherapy for the particular disease or condition being treated.

EXAMPLES

Example 1

Biacore Analysis of Humanized Z270

Humanized Z270 (humZ270) is described in U.S. Pat. No. 8,206,709 (Novo Nordisk), the disclosure of which is incorporated herein by reference. As described in U.S. Pat. No. 8,206,709, HumZ270 VKI_O2/JK4 light chain and various heavy chain acceptor frameworks were produced as human IgG4 antibodies. Heavy chain frameworks included "VH1" based on VH1_18/JH6; "VH5" based on VH5_a; "VH6" based on VH5_51; "VH7" based on VH1_f; and "VH8" based on VH1_46, all with a JH6 J-segment. The antigen-binding properties were analyzed on a Biacore T100 (Biacore AB, Uppsala, Sweden). The antigen was in the form of a single-chain NKG2A-CD94-mFc construct was covalently immobilized on the sensor CM5 chip (Biacore AB, Uppsala, Sweden) via amine groups using 1-ethyl-3-(3-dimethylaminopropyl) carbodiimide hydrochloride (EDC) and N-hydroxysuccinimide (NHS). The immobilization level was targeted at 300 RU. Z270 antibody variants were diluted to a concentration series (0.157, 0.313, 0.625, 1.25, 2.5 nM) in the running buffer HBS-EP (10 mM HEPES pH 7.4, 150 mM NaCl, 3 mM EDTA, 0.005% (v/v) Tween-20). All the samples were then injected over the immobilized antigen for 2 min at the flow rate of 40 ul/min. Subsequently, the running buffer was injected for 3 min at 40 ul/min for antibody dissociation analysis. After each run, the regeneration buffer (10 mM NaOH, 500 mM NaCl) was injected (30 seconds, 10 ul/min) to completely strip the remaining antibodies off the antigen. Data were evaluated with Biacore T100 evaluation software.

The affinity of humanized Z270 VH1 was determined as 67 pM. Affinities of the VH5, VH6, VH7 and VH8 were comparable.

TABLE

| humZ270 | | | |
|---|---|---|---|
| ka (1/Ms) | Kd (1/s) | KD (M) | Chi$^2$ (RU$^2$) |
| 7.492E+6 | 4.982E-4 | 6.650E-11 | 0.044 |

Example 2 humZ270 is a Competitive CD94/NKG2A Antagonist

As described in U.S. Pat. No. 8,206,709, to test whether humZ270 prevents ligand (i.e. HLA-E) binding to CD94/NKG2A, humZ270 was tested for the ability to prevent the binding of HLA-E tetramers to CD94/NKG2A over-expressing Ba/F3 cells (Ba/F3-CD94/NKG2A). humZ270VL1/VH1 having the respective heavy and light chains of SEQ ID NOS: 3 and 7 was used in this Example, and unless indicated to the contrary, this antibody was also used as humZ270 for all other Examples below. For this, Ba/F3-CD94/NKG2A were incubated with 1) various concentrations of humZ270 or 2) first incubated with a saturating concentration of HLA-E tetramers (4.7 μg/ml) and then incubated with various concentrations of humZ270. All incubations were performed in tissue-culture medium containing 2% FCS, on ice. Subsequently, cells were incubated with APC-conjugated secondary antibodies specific for mouse Ab's, and analyzed by flowcytometry using a BD Biosciences FACSarray.

humZ270 efficiently binds Ba/F3-CD94/NKG2A cells in a concentration dependent fashion (diamonds). However, when cells were pre-incubated with HLA-E tetramers, humZ270 was prevented from binding to Ba/F3-CD94/NKG2A cells. Thus HumZ270 and HLA-E bind overlapping epitopes on CD94/NKG2A. Therefore, the CD94/NKG2A-inhibitory effect of humZ270 in NK-cytotoxicity assays is likely a consequence of preventing the ability of HLA-E inducing negative signals to cytotoxic lymphocytes via CD94/NKG2A. As such, humZ270 can be considered a competitive CD94/NKG2A antagonist.

Example 3

Distribution of NK and T Cell Subsets in C57/bl6 Mice Bearing rma-rae1 Tumor Based on NKG2A Expression To further investigate the expression of NKG2A in tumor settings, distribution of NKG2A was studied on NK and T cell subsets in mice. Lymphocytes were taken from spleen, from tumor draining lymph nodes, as well as from within solid tumors.

C57/BL6 mice were engrafted (sc) with RMA-Rae clone 6 (2 million cells). These tumor cells express CD94/NKG2A ligand, Qa-1. Mice were sacrificed at day 12 with a mean tumor volume: 723 mm$^3$, SD: 161 mm$^3$, n=4. Following cell suspension preparation from spleen, LN and tumor, cells were stained as follows: CD3e PerCP Cy5.5, NKP46 Alexa 647, NKG2A/C/E FITC, CD8 Pacific Blue.

Results, shown in Tables 1-3, revealed NKG2A-expressing NK and CD8+ T lymphocytes are found in significant percentages within the tumor environment with NKG2A+ CD8+ T cells being present in high percentages in the tumor environment but not in the spleen or tumor draining lymph nodes. In the NK cell subset, cells in both the draining lymph nodes and spleen were about half NKG2A-positive and half NKG2A-negative. In the T cell subset most cells were NKG2A-negative (only 1.1% in lymph nodes and 4.7% in spleen are NKG2A$^+$). In the CD8 T cell subset, most cells were again NKG2A-negative (only 1.6% in lymph nodes and 3.9% in spleen are NKG2A$^+$). However, while almost no CD8 T cells outside the tumor had NKG2A expression, tumor infiltrating CD8 T cell subset had a mean of 26.3% NKG2A+ positive cells. Among the CD8$^-$ T cell subset, there was little difference in NKG2A expression observed between TILs and spleen or lymph node cells, as only 5.1% of CD8$^-$ T cells in the tumor expressed NKG2A.

TABLE 1

| | Spleen | | |
|---|---|---|---|
| | % NK NKG2A+ | % T NKG2A+ | % T CD8+ NKG2A+ |
| Mice1 Spleen | 41.864 | 4.54 | 4.95 |
| Mice2 Spleen | 46.198 | 6.25 | 3.36 |
| Mice4 Spleen | 44.49 | 3.37 | 3.45 |
| Mean | 44.2 | 4.7 | 3.9 |
| SD | 2.2 | 1.45 | 0.89 |

TABLE 2

| | Tumor Draining Lymph Nodes | | |
|---|---|---|---|
| | % NK NKG2A+ | % T NKG2A+ | % T CD8+ NKG2A+ |
| Mice1 LN | 45.95 | 0.5 | 2.1 |
| Mice3 LN | 55.10 | 0.7 | 3.1 |
| Mice4 LN | 49.11 | 0.6 | 0.8 |
| Mean | 50.05 | 1.1 | 1.6 |
| SD | 4.65 | 1.1 | 1.3 |

TABLE 3

| | Tumor Infiltrating Lymphocytes | | |
|---|---|---|---|
| | % NK NKG2A+ | % T NKG2A+ | % T CD8+ NKG2A+ |
| Mice1 TIL | 52.2 | 2.89 | 26.8 |
| Mice2 TIL | 44.5 | 8.22 | 26.05 |
| Mice3 TIL | 52 | 9.3 | 34.31 |
| Mice4 TIL | 55 | 0 | 17.9 |
| Mean | 50.9 | 5.1 | 26.3 |
| SD | 4.5 | 4.4 | 6.7 |

Example 4

In Vitro Receptor Saturation: Binding of Humanized Anti-NKG2A Antibody IPH2201 to NKG2A+ NK Cells in Whole Blood Receptor occupancy of anti-NKG2A was assessed in vitro in human blood, providing a prediction of the pharmacokinetics of anti-NKG2A in human patients. This study was aimed to estimate ex vivo the cellular affinity in whole blood of HumZ270 as well as the absolute number of available NKG2A receptors per µl of whole blood and also per cell in humans. The affinity and total number of receptors may impact both pharmacokinetics (PK) and pharmacodynamics (PD) of the mAb in humans. These data will be used as input for the PK/PD model which will be used for designing the first human dose trial. Human whole blood was collected from each donor and processed immediately. A titration of humZ270 was done in whole blood from 8 volunteers (mAb incubated for 30 minutes at room temperature (RT). Fifteen mAb concentrations were tested to cover the full range of binding between 0 and 100% of maximal binding, going from 90 µg/ml to 0.000019 µg/ml (⅓ serial dilution, 15 points and 0). Samples were processed to remove red blood cells and fix the cells and acquired on a cytometer. Calibrating beads were used to transform MFI results into MESF (Molecule of Equivalent Soluble Fluorochrome). Gating was done on CD45+ lymphocytes expressing NKG2A.

Three tubes were dedicated to absolute counting of lymphocyte subsets using flow-count beads added into the blood. First, a titration was done using humZ270, in which bound humZ270 was be detected using a PE-coupled anti-hIgG4 secondary antibody. A titration was also performed with PE-coupled humZ270 and compared to titration done with bound humZ270 in order to examine the effect of the coupling to PE on the pharmacological properties of humZ270 and for evaluating the total number of receptors for a saturating concentration of humZ270.

Analysis focused on NKG2A+ cell subsets, i.e. NK cells and T cells. These subsets of lymphocytes do not all express NKG2A and therefore a NKG2A− subset for each population of interest were studied and compared to the NKG2A+ subset. The cell populations are defined as follows:

Lymphocytes: defined on a CD45/SSC plot, according to their granularity and size and CD45 expression
Human NK lymphocytes: CD3-CD56+ cells among lymphocytes
CD8 T cells: CD3+ CD8+ cells among lymphocytes
NKG2A+ lymphocytes: NKG2A+ cells among lymphocytes.

The total Mean Fluorescence Intensity (MFI) was recorded for each population. Calibrating beads was used to express Fluorescence in PE channel as MESF. The main populations of interest in this study are NKG2A+ lymphocytes mainly including NK cell.

Results showed that human anti-NKG2A mAb (humZ270) binds to two subsets of peripheral blood lymphocytes: NK and CD8+ T cells.

Results are summarized in FIG. 1. HumZ270, also referred to as IPH2201, is shown at different concentrations (ng/ml) listed on the x-axis and MESF signal for receptor binding is shown on the y-axis. The antibody had a binding affinity (EC50) of about 4 ng/mL for NKG2A+ cells ($K_D$~4 ng/mL). This $K_D$ is consistent with $K_D$ values observed in other assays, notably affinity for binding to PBMC and affinity for recombinant NKG2A in Biacore assays. The $K_D$ for full receptor occupancy (the EC100) was about 100 ng/ml.

Example 5

Receptor Saturation of IPH2201 in a Human Phase I Clinical Trial in Rheumatoid Arthritis HumZ270, a human IgG4 antibody was produced with a heavy chain having a serine to proline mutation in residue 241 of the heavy chain (S241P mutation), corresponding to position 228 according to the EU-index, in order to maintain high affinity bivalent binding in vivo. The safety profile of humZ270 (IPH2201) was explored in a double-blind, placebo-controlled dose-escalation phase I trial in 92 patients with stable and controlled rheumatoid arthritis. In this three-armed phase I trial, Z270 or placebo was administered as single-dose i.v. up to 10 mg/kg, or single-dose s.c. or multiple-dose s.c. (four administrations given with 2-week intervals) up to 4 mg/kg. The dosages tested as single dose by i.v. were: 0.0002, 0.001 mg/kg, 0.005 mg/kg, 0.025 mg/kg, 0.1 mg/kg, 0.4 mg/kg, 1.1 mg/kg, 3.5 mg/kg and 10 mg/kg. All patients were followed for a minimum of 12 weeks. The safety profile was very favorable. The MTD was not reached. There were no SUSAR, no drug-related serious adverse events, no infusion related reaction and no immune related adverse event. Nasopharyngitis and headache were the two most frequently reported adverse events.

Receptor saturation was assessed using a conventional sandwich ELISA format with a mouse Fc human NKG2A fusion protein used to capture the humZ270 antibody. After incubation with serum samples containing humZ270 antibody, bound antibody (the analyte in this study) is detected using a biotinylated mouse anti human IgG4. HRP labelled avidin is added to tag the solid phase bound biotinylated anti-human IgG4 and a colorimetric HRP substrate (TMB) is used for end point detection. The optimal dose and dosing frequency for the Anti-NKG2A (IPH2201) dose levels to be used in the clinical trials that would provide substantially full receptor saturation was predicted using a PK/PD model developed using pharmacokinetic software package (WinNonLin 6.3.0.395, Pharsight Corporation), model based on clinical data from IPH2201 phase I in RA patients. The dosing frequency in clinical therapy using IPH2201 depends on the steady state plasma concentration needed for saturation as well as the clearance and volume of distribution of IPH2201.

Preliminary PK data and NCA analysis for IPH2201 phase I clinical trial, i.v. injection, enabled us to estimate the PK parameters for the PK model. Nominal times were used. A standard 2-compartment model was selected, with $1^{st}$ order elimination and a non Linear Target Mediated Drug Disposition modelled by Michaelis Menten kinetic. A dose-dependent clearance was observed in NCA analysis and applied to this model, with clearance decreasing with increasing doses under 0.4 mg/kg, then remaining constant for higher doses. This preliminary PK model is consistent with known PK characteristics for IgGs for which dose dependency reflects target receptor (at low doses) and FcRn receptor (high doses) saturations (Brambell).

A population PD modelling was performed based on preliminary NKG2A occupancy data available from the ongoing phase I clinical trial.

A sigmoid Emax model was used to fit the plasma concentration-effect relationship. The model was characterized by an $EC_{50}$, defined as the serum drug concentration to reach 50% of $E_{max}$, i.e. 50% of NKG2A occupancy here.

Figure 2:
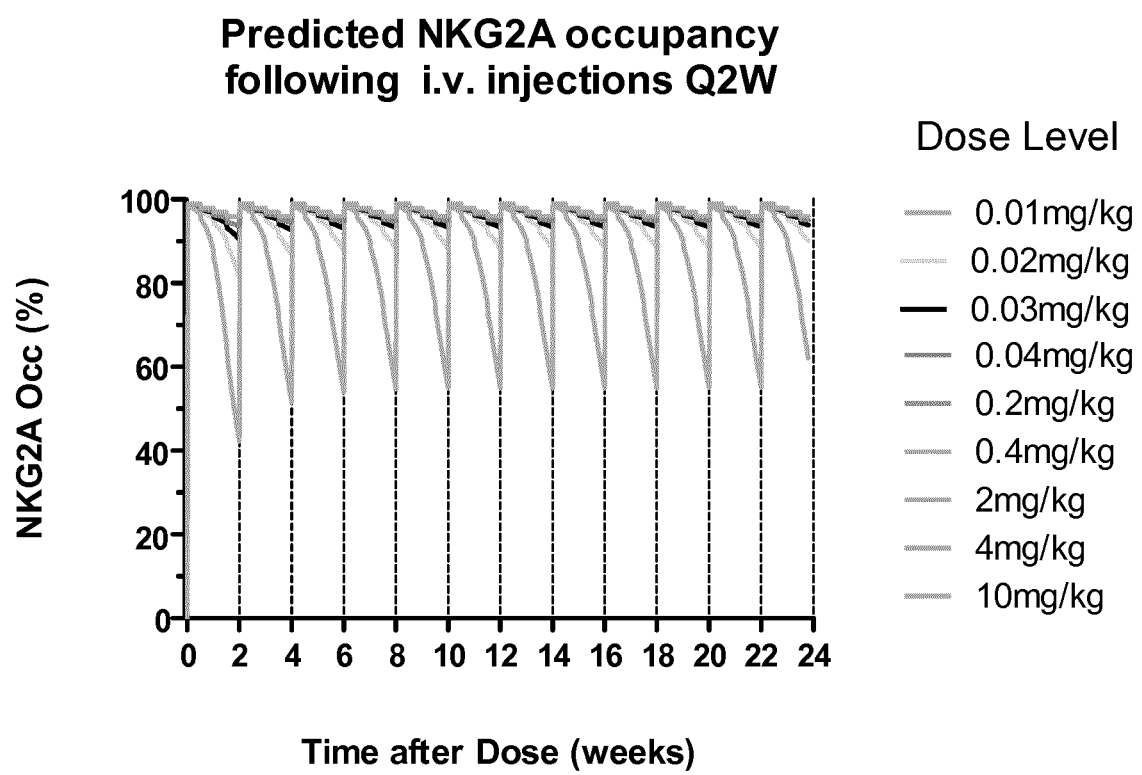
FIG. 2 shows predicted receptor occupancy of anti-NKG2A antibody based on human patients treated with a single dose of HumZ270 in a 92-patient Phase I trial. Substantially complete (at least 90%) receptor saturation of NKG2A+ cells can be achieved by administering 0.03 mg/kg every two weeks. Receptor saturation is greater with increasing doses, the plotted line in the figure having lowest receptor saturation corresponds to the lowest dose (0.01 mg/kg); each incremental higher dose level corresponds to the plotted line having the next higher receptor saturation, the line corresponding to the highest dose (10 mg/kg) has the highest receptor saturation. A dose of 0.1 mg/kg can be administered every four weeks to maintain substantially complete saturation of NKG2A.

However, when PD data were plotted against PK data, it was observed that as time after dosing increased, maximum NKG2A occupancy (Emax) obtained for the highest IPH2201 concentrations decreased in a time dependant linear manner, with no impact of the dose. Similarly, the EC50 seemed to linearly increase with time. In order to model this observation in NKGA2 occupancy profile, a decrease in Emax and an increase in EC50 with time were included to describe the NKG2A occupancy data.

$$\% \ NKG2A \ occupancy = (E_{max} - (E_{max}\text{Fall} \times \text{TSLD})) \times C^\gamma / ((EC_{50} + EC_{50}\text{inc} \times \text{TSLD})^\gamma + C^\gamma)$$

Where TSLD=Time Since Last Dose; $E_{max}$=100%; $E_{max}F_{all}$=Rate of Decrease in Emax with time; $EC_{50}$inc=Rate of Increase in $EC_{50}$ Results of modelling are shown in FIG. 2, substantially complete (at least 90%) receptor saturation of NKG2A+ cells can be achieved by administering 0.03 mg/kg every two weeks. A dose of 0.1 mg/kg can be administered every four weeks to maintain substantially complete saturation of NKG2A. If saturation in the extravascular tissue (e.g. a solid tumor) is desired, an approximately 10-fold higher dose is believed to be needed, translating to a dose of about 0.4 mg/kg every two weeks, 1 mg/kg every four weeks.

The results for saturation of NKG2A receptors from this human clinical trial was consistent with the in concentration of anti-NKG2A required for full receptor occupancy (the EC100) determined in vitro (see Example 4).

Example 6

CD107 Response to NKG2A Blockade Using IPH2201

Autologous in vitro experiments using effector and target cells were performed in order to assess the killing mediated by cytokine-activated purified NK cells (effector cells) in 12 human individuals. For three donors, assessment of CD107 mobilization and occupancy was performed in parallel. The target cells were autologous SEB blasts. This killing is considered to be mediated by NK cells, and it can be specifically increased by an anti-NKG2A antibody as it is expected to counteract the inhibitory signal from HLA-E. A concentration-range response with antibody humZ270 was performed in a 4-hour cytotoxicity assay. It was chosen to use purified NK cells and a CD107 mobilization assay based on the experimental results generated. First, the FACS-based CD107 assay enables the specifically study of the cytotoxic response of NK cells expressing NKG2A and to compare it to NK cells not expressing NKG2A. An alternative protocol such as chromium release assays would not have allowed discriminating the effect depending on NKG2A expression which is an issue in donors with a low percentage of NKG2A+ cells.

Autologous SEB blasts were generated by incubating frozen PBMC with 200 IU/ml recombinant human IL-2 (Proleukin) and 100 ng/ml SEB (Staphylococcal Enterotoxin B, Sigma) for 4 days in complete medium (RPMI, 10% FCS, Penicillin/Streptomycin). Then CD4 T cells were negatively selected by using the "Stemsep negative selection human CD4 T cell enrichment kit" (article number #14052A). Purity was assessed by FACS and HLA-E expression is measured with the PE-conjugated anti-HLA-E clone 3D12 (E-Biosciences). T CD4 SEB blasts were considered as a good model for generating autologous cells mimicking autoreactive T CD4+ cells.

Purified NK cells were prepared from frozen PBMC: Human NK purification with Stem Sep system, and cultured O/N in complete medium supplemented with 10 IU/ml recombinant IL-2. PBMC were prepared from collected blood. Blood was qualified for transfusion, donors were thus anonymous and supposedly healthy. PBMC were prepared, aliquoted and stored in nitrogen tanks prior to the study.

Calculations of Kd for receptor saturation and $EC_{50}$ for CD107 mobilization were performed in Graph Pad Prism software using a non-linear regression fit with four parameters. In order to estimate the affinity constant Kd from the titration curves of anti-NKG2A (IPH2201) binding to purified NK cells, values for the 30 and 90 µg/ml were excluded because some artifacts were observed at these concentrations.

Figure 3A:
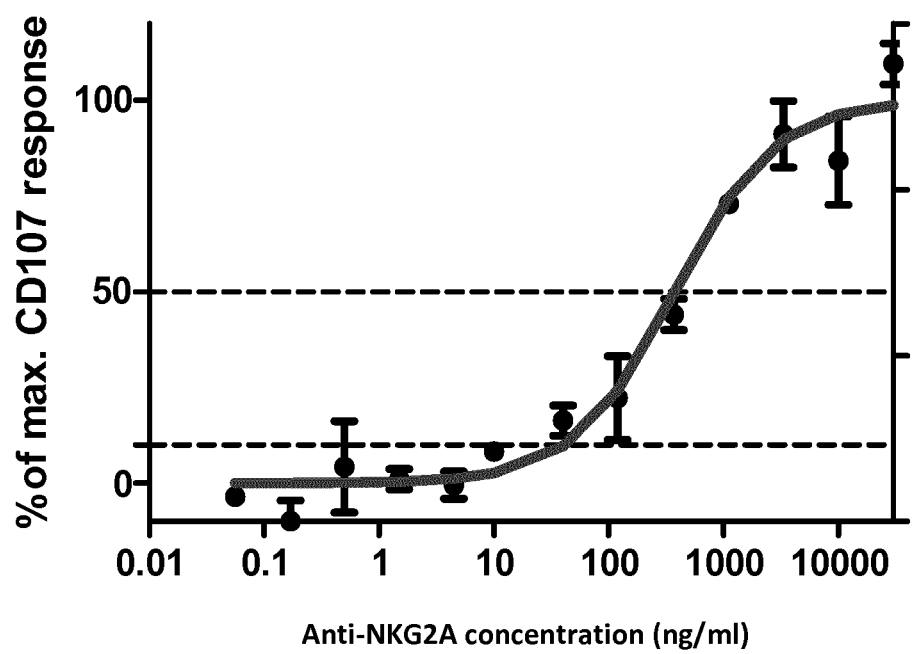
FIG. 3A shows results from an autologous cellular assay, showing that the concentrations of anti-NKG2A required for efficacy (NKG2A blockade in the presence of cells expressing its HLA-E ligand) are 100-fold higher than concentrations providing full receptor saturation. The EC50 concentration (the amount that provides a 50% of maximum) in the CD107 mobilization assay was determined to be about 400 ng/ml, and the EC100 was about 10,000 ng/ml (10 µg/ml).

Results are summarized in FIG. 3A. Surprisingly, the concentrations of anti-NKG2A required for efficacy (blockade) are 100-fold higher than concentrations providing full receptor saturation. The EC50 concentration (the amount that provides a 50% of maximum) in the CD107 mobilization assay was determined to be about 400 ng/ml, and the EC100 was about 10,000 ng/ml (10 µg/ml). In contrast, as shown in Example 4, the EC50 concentration for receptor saturation is about 4 ng/ml and the EC100 is about 100 ng/ml, a concentration also corroborated by data from the Phase I clinical trial (see Example 5).

For the three donors with parallel assessment of CD107 mobilization and occupancy, the individual $EC_{50}$ values for CD107 were approximately 100-fold higher than the individual Kd for receptor saturation. The same ratio was observed when evaluating all data (median Kd for receptor saturation 0.005 µg/ml, n=5, median EC50 for CD107 mobilization 0.40 µg/ml, n=9). This suggests that donors generally have comparable receptor affinities for IPH2201 and that the relationship between receptor saturation and biological activity is similar.

Example 7

Effect of HLA-E Expression Levels on CD107 Response to NKG2A Blockade

The 100-fold difference between Kd obtained for receptor saturation and the EC for CD107 mobilization could potentially be explained by membrane-bound HLA-E on the target cells in the CD107 assay which engages NKG2A on the NK cells with a high avidity, requiring more IPH2201 to reach functional saturation of the receptor compared to receptor saturation experiments in which there is no HLA-E involved.

To investigate this possibility, the EC observed for biological effect in autologous SEB blasts in Example 6 was compared to that of cells having different levels of expression of HLA-E. Human K562 cells transfected with HLA-E were selected as high HLA-E expressing cells. The FACS-based CD107 assay was performed using purified NK cells as described in Example 6.

In each experiment, autologous CD4+ SEB blasts and a selected K562-HLA-E clone were tested for HLA-E expression using the anti-HLA-E mAb, 3D12, coupled to PE. HLA-E expression on K562HLA-E transfectants was at least 20 fold higher than the constitutive HLA-E expression observed on autologous SEB blasts. The purity of the SEB blasts was 96%±0.818 (SD, n=12, range 94.6%-97.1%). The expression of HLA-E on T CD4 SEB blasts and K562-HLA-E was similar between all donors.

Corroborating this observation of a 100-fold difference between Kd obtained for receptor saturation and the EC for CD107 mobilization, the lower EC observed for biological effect on the SEB blasts (median 0.40 µg/ml) compared to the EC50 on K562-HLA-E transfectants (median 4.1 µg/ml) can be explained by the at least a 20-fold difference in HLA-E expression at the cell surface. In this case, as HLA-E is expressed at higher densities on K562-HLA-E transfectants, higher amount of IPH2201 are required to compete with HLA-E when compared to autologous SEB blasts.

Example 8

Pharmacokinetic Model Prediction for Repeated Injections of IPH2201

Based on the EC for CD107 mobilization observed for autologous (SEB) cells in Example 7, and with the incorporation of the blood concentration results from the Phase I trial described in Example 5, modelling was performed to determine the optimal dosing frequency for the Anti-NKG2A (IPH2201) dose levels to be used in the clinical trials that would provide efficacy.

The optimal dose and dosing frequency for the anti-NKG2A (IPH2201) dose levels to be used in the clinical trials was predicted using a PK/PD model developed using pharmacokinetic software package (WinNonLin 6.3.0.395, Pharsight Corporation), model based on clinical data from IPH2201 phase I in RA patients. The dosing frequency in clinical therapy using IPH2201 depends on the steady state plasma concentration needed as well as the clearance and volume of distribution of IPH2201.

Preliminary PK data and NCA analysis for IPH2201 phase I clinical trial, i.v. injection, enabled us to estimate the PK parameters for the PK model. Nominal times were used. A standard 2-compartment model was selected, with $1^{st}$ order elimination and a non Linear Target Mediated Drug Disposition modelled by Michaelis Menten kinetic. A dose-dependent clearance was observed in NCA analysis and applied to this model, with clearance decreasing with increasing doses under 0.4 mg/kg, then remaining constant for higher doses. This preliminary PK model is consistent with known PK characteristics for IgGs for which dose dependency reflects target receptor (at low doses) and FcRn receptor (high doses) saturations (Brambell).

Based on preliminary PK and PD data from clinical phase I trial, the following PK and PD parameters best fitted the observed data:

| Dose Level | CL (L/h) |
| --- | --- |
| 0.02 | 0.018 |
| 0.04 | 0.015 |
| 0.2 | 0.010 |
| 0.4 | 0.008 |
| 2 | 0.006 |
| 4 | 0.006 |
| 10 | 0.006 |

| Parameter | Value | Unit |
| --- | --- | --- |
| Ka | 0.00426 | h−1 |
| F (Biodispo) | 0.826 | |
| CL for 1 mg/kg | 0.006 | L/h |
| V1 | 2.8 | L |
| V2 | 1.99 | L |
| Q | 0.0109 | L/h |
| Vm | 0.223 | mg/wk |
| Km | 21.7 | ng/ml |

Figure 3B:
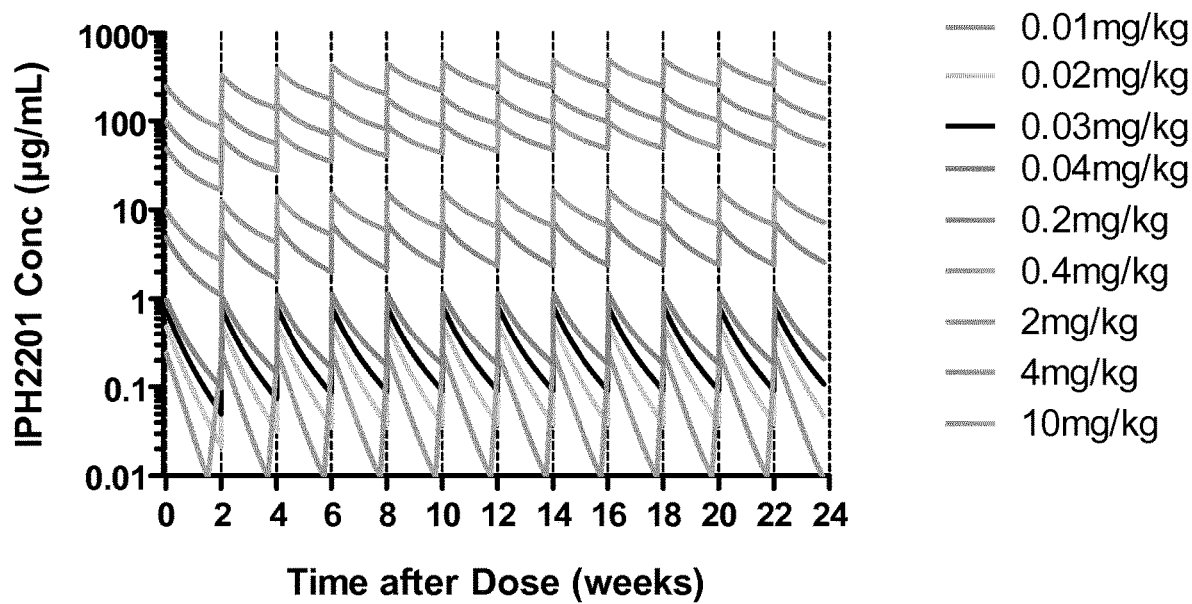
FIG. 3B shows the predicted IPH2201 (anti-NKG2A) blood concentration following two-weekly i.v. injections, based on preliminary PK data and NCA analysis from a IPH2201 phase I clinical trial. Different blood concentrations reached with different dosages administered by i.v. every two weeks. IPH2201 concentration is greater with increasing doses, the plotted line in the figure having lowest blood concentration corresponds to the lowest dose (0.01 mg/kg); each incremental higher dose level corresponds to the plotted line provides the next higher blood concentration, the line corresponding to the highest dose (10 mg/kg) provides the highest blood concentration. The dose of 4 mg/kg provided an initial (peak) blood concentration of about 100 µg/ml, i.e. at about the $EC_{100}$ for efficacy in tissues, and a continued (minimum) blood concentration above 30 µg/ml up to the two week time point, or, as of the fourth dose a continued (minimum) blood concentration of approximately 100 µg/ml. The dose of 10 mg/kg provided a continued (minimum) blood concentration approximately 100 µg/ml.

FIG. 3B shows different blood concentrations reached with different dosages administered by i.v. every two weeks. Dose levels were 0.01, 0.02, 0.03, 0.04, 0.2, 0.4 mg/kg, 2 mg/kg, 4 mg/kg and 10 mg/kg body weight. The lines in FIG. 3B correspond, from bottom to top, to increasing doses of IPH2201, where the lowest dose corresponds to the lowest line at the bottom of the chart to the highest dose at the top of the chart. The dose of 0.01 mg/kg provided an initial (peak) blood concentration of about 0.2 µg/ml. The dose of 0.04 mg/kg provided an initial (peak) blood concentration of about 1 µg/ml, i.e. above the $EC_{50}$ for efficacy of 400 ng/ml, but after two weeks was below the $EC_{50}$. The dose of 0.4 mg/kg provided an initial (peak) blood concentration of about 10 µg/ml, i.e. at about the $EC_{100}$ for efficacy in circulation, and a continued blood concentration above 3 µg/ml up to the two week time point. The dose of 4 mg/kg provided an initial (peak) blood concentration of about 100 µg/ml, i.e. at about the $EC_{100}$ for efficacy in tissues, and a continued blood concentration above 30 µg/ml up to the two week time point. However, when the dose of 4 mg/kg is administered in repeat dosing, the fourth dose provides continued blood concentration of approximately 100 µg/ml. The dose of 10 mg/kg provided a continued blood concentration approximately 100 µg/ml.

Figure 3C:
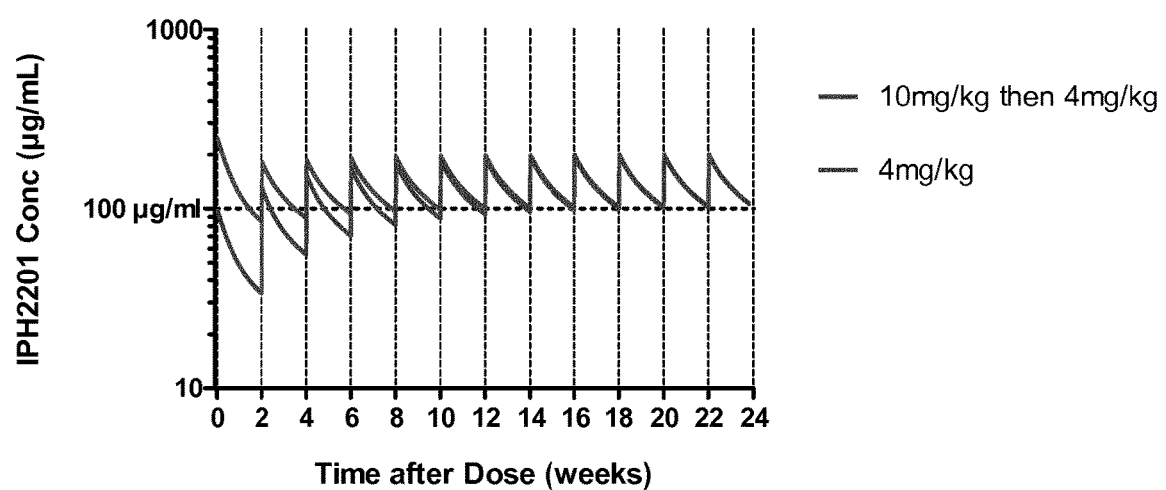
FIG. 3C shows predicted IPH2201 blood concentration following two-weekly i.v. injections with a loading dose of 10 mg/kg body weight followed by a maintenance dose of 4 mg/kg body weight (shown as the upper line), providing an initial and continued blood concentration approximately 100 µg/ml. For purposes of comparison, a constant dose of 4 mg/kg is shown (the lower line in the figure) which provides for a continued (or minimal) blood concentration of at least 30 µg/ml at two weeks.

FIG. 3C shows different blood concentrations reached with different dosages administered by i.v. every two weeks, when a loading dose and maintenance dose are used. In a two-week dosing frequency, a loading dose of 10 mg/kg body weight followed by a maintenance dose of 4 mg/kg body weight (the upper line in FIG. 3C) provides provided an initial and continued blood concentration approximately 100 µg/ml. For purposes of comparison, a constant dose of 4 mg/kg is shown as the lower line in FIG. 3C, which provides for a continued (or minimal) blood concentration of at least 30 µg/ml between the initial and subsequent injection at two weeks, a continued (or minimal or remaining) blood concentration of at least 50 µg/ml at two weeks after the second injection, a continued (or minimal or remaining) blood concentration of at least 60-70 µg/ml at two weeks after the third injection.

Example 9

Effect of a Dose-Response of Anti-NKG2A on NK Cells Activation

Immunotherapeutic approaches for HNSCC are particularly complicated by the profound immune suppression that is induced by HNSCC, which potentially decreases the effectiveness of immune stimulatory efforts (see, e.g., Duray et al. (2010) Clin. Dev. Immunol. 2010: 1-15). The goal of this experiment was to explore whether an anti-NKG2A antibody that targets NKG2A is able to eliminate HNSCC cells.

Effect of a dose-response of anti-NKG2A on NK cells activation was determined by analysis of CD107 and CD137 expression. CD107 mobilization at 4 hours is a marker of the release of lytic granules by NK cells (Alter et al., (2004) J Immunol Methods 294(1-2): 15-22). Increase in CD137 expression at 24 hours is correlated with the activation of several lymphocytes including NK cells (Kohrt et al. (2011)

Blood 117(8):2423-2432). Analysis of CD107 and CD137 expression was performed on NK cells expressing or not expressing NKG2A (NKG2A+ NK cells or NKG2A− NK cells respectively). Since the antibody is targeting NKG2A, its effect is expected to be seen only on NKG2A+ NK cells, and thus NKG2A− NK cells can be regarded as an internal control in the experiments.

The effector cells used were freshly isolated PBMC from healthy volunteers and target cells were HNSCC cell lines or clones of K562 cell line transfected with HLA-E. Cells were numerated and passed every two days in complete medium. Viability was measured and had to be over 90%. They were kept in culture up to 12 passages. The day before of the experiment, cells were counted and adjusted to 100,000 cells/wells. Viability was measured and had to be over 90%.

The K562 cell lines were K562 clone E6 (HLA-E positive, CD32low) and K562 clone F7 (HLA-E negative/low, CD32low). Human head and neck cancer cell lines were screened by flow cytometry for HLA-E expression (see Table C, below). Three cell lines were selected for functional tests: FaDu (ATCC #HTB-43), H-N (DSMZ #ACC 417) and CAL-27 (DSMZ #ACC 446).

TABLE C

| Cell line | HLA-E expression Mean HLA-E/IC MFI ratio | # exp. | Cell type | Source |
|---|---|---|---|---|
| H-N | 2.8 | n = 2 | Oral squamous cell carcinoma | DSMZ, Germany |
| Detroit 562 | 2.7 | n = 1 | Pharynx carcinoma (metastatic site: pleural effusion) | ATCC, USA |
| SCC-9 | 3.7 | n = 1 | Tongue squamous carcinoma | ATCC, USA |
| A-253 | 3.5 | n = 1 | Submaxillary salivary gland; epidermoid carnoma | ATCC, USA |
| FaDu | 5.2 | n = 2 | Pharynx squamous cell carcinoma | ATCC, USA |
| BICR6 | 1.8 | n = 1 | Hypopharynx squamous cell carcinoma | Public Health England, UK |
| BICR16 | 2.4 | n = 1 | Tongue squamous carcinoma | Public Health England, UK |
| CAL-27 | 4.0 | n = 2 | Tongue squamous carcinoma | DSMZ, Germany |
| BICR10 | 2.3 | n = 1 | Buccal mucosa squamous carcinoma | Public Health England, UK |

The effector cells used were freshly isolated PBMC from healthy volunteers. Target cells were the HNSCC cell lines (FaDu, H-N and CAL-27), and clones of K562 cell line transfected with HLA-E (Clone E6=HLA-E$^+$, clone F7=HLA-E$^-$) as an E:T ratio 2.5/1. Read out was CD107 at 4 hours vs. CD137 at 24 hours. 7 donors (FaDu and H-N) and 2 donors (CAL-27) were tested. Anti-NKG2A antibody humZ270 VH1 whose heavy chain amino acid sequence is shown in SEQ ID NO: 3 and whose light chain amino acid sequence is shown in SEQ ID NO: 7 was used at a final concentration of 10 µg/mL.

Figure 4A:
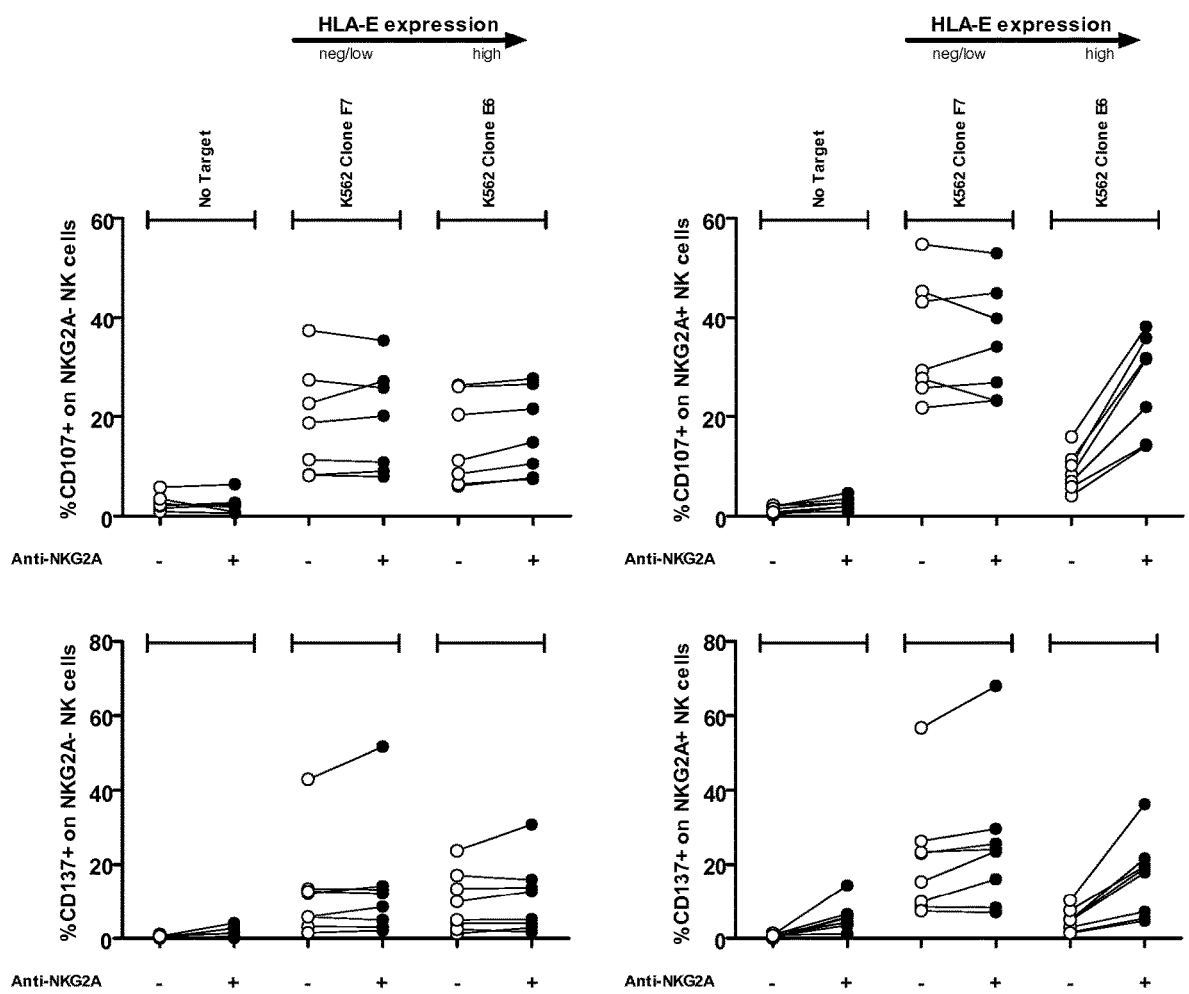
FIGS. 4A and 4B shows ability of anti-NKG2A to enhance recognition of HNSCC cell lines by NK cells. CD107 (Top) and CD137 (Bottom) FACS read-outs on NKG2A− NK (left) or NKG2A+ NK cells (right) are indicated, in presence of indicated target HNSCC cell lines and in presence or not of anti-NKG2A at a concentration of 10 µg/mL. The cell lines are ordered from left to right according to level of HLA-E surface expression. Each dot represents PBMC from a healthy volunteer.
Figure 4B:
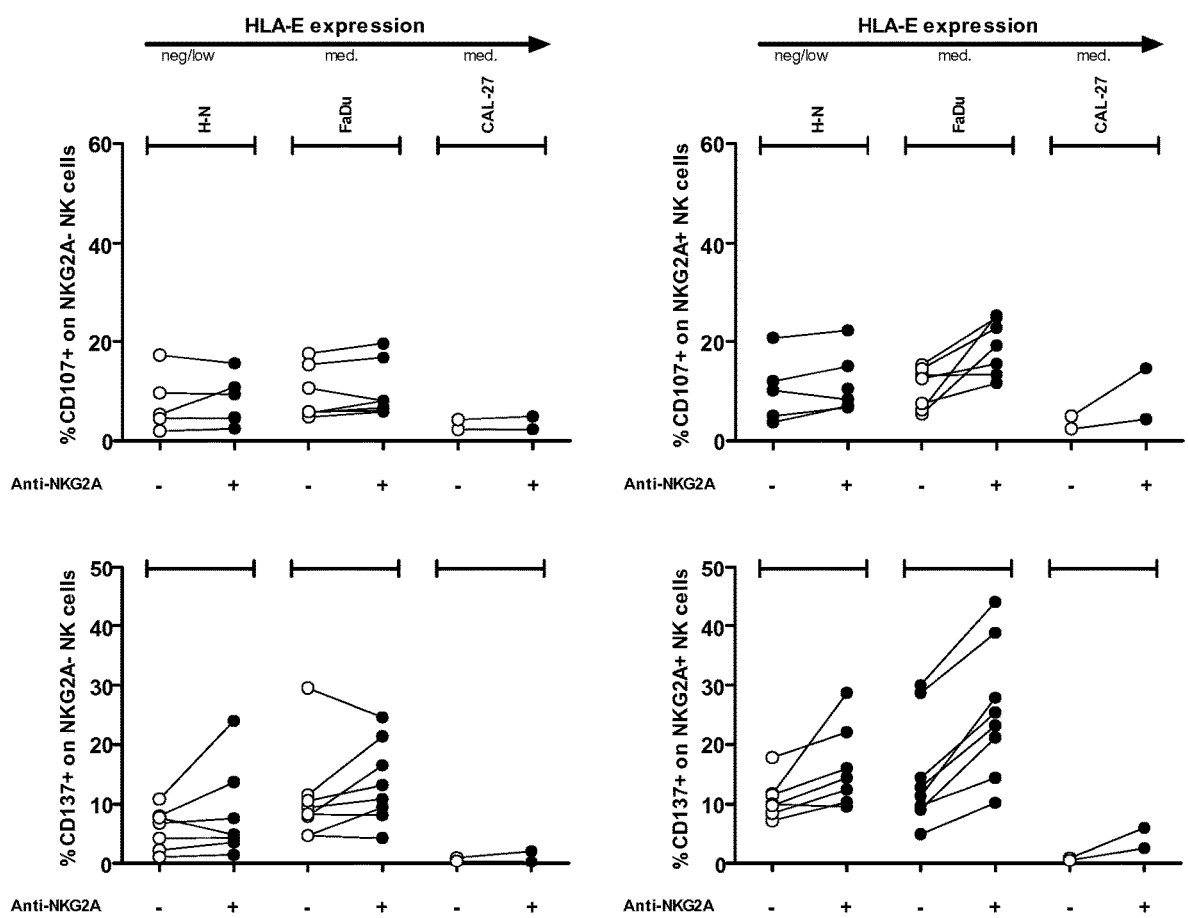

FIGS. 4A and 4B show CD107 (Top) and CD137 (Bottom) FACS read-outs on NKG2A− NK (left) or NKG2A+ NK cells (right) in presence of controls or indicated target cell lines and in presence or not of anti-NKG2A at a concentration of 10 µg/mL. The cell lines are ordered from left to right according to level of HLA-E surface expression. Each dot represents PBMC from a healthy volunteer. FIG. 4B shows HNSCC cell lines and demonstrates anti-NKG2A can restore lysis of HNSCC with endogenous HLA-E expression or of K562 transfected with HLA-E. This effect is only seen on NKG2A positive NK cells and is dependent on the level of expression of HLA-E. Indeed, anti-NKG2A effect is seen on cell lines with medium to high HLA-E level of expression.

Anti-NKG2A can induce the NK-mediated lysis of HLA-E expressing cell lines by blocking the interaction of the inhibitory receptor NKG2A with HLA-E. This effect is observed on K562 cell line transfected with HLA-E, but more importantly on HNSCC cell lines with endogeneous HLA-E expression such as FaDu and CAL-27 cell lines. The extent of anti-NKG2A effect depends on the level of HLA-E expression at the cell surface of the target cells.

Example 10

Combined Effect of an Optimal Dose of Anti-NKG2A with Sub-Optimal Doses of Cetuximab Epidermal growth factor receptor (EGFR), (also ErbB-1; HER1 in humans), is a ubiquitously expressed transmembrane glycoprotein in the ErbB/HER family of receptor tyrosine kinase. High expression of EGFR occurs in most epithelial malignancies including HNSCC and is associated with a poor prognosis. Its activation through natural ligands leads to the initiation of intracellular signaling pathways that regulate the activation of cell proliferation, invasion, angiogenesis and metastasis driving tumor growth.

The anti-EGFR monoclonal antibody cetuximab is thought to act through blocking oncogenic signaling of the EGF receptor pathway and by inducing Fcγ receptor-mediated antibody dependent cellular cytotoxicity (ADCC). In HNSCC however, ADCC may be affected by the profound immune suppression that is induced. At the same time, blocking oncogenic signaling of the EGF receptor pathway results in posttranscriptional regulation in tumor cells of major histocompatibility complex (MHC) class I-related antigens of the MICA/B and ULBP protein families which are recognized by the activating receptor NKG2D on NK cells and subsets of T cells. In particular, the expression by tumor cells of these stress-related antigens which are the natural ligands of NKG2D is decreased by clinical EGFR inhibitors, thus potentially decreasing the tumor cells' visibility to NK and T cells (Vantourout et al., Sci. Transl. Med. 6: 231ra49 (2014).

This experiment was designed to explore the effect of an EGFR inhibiting antibody on the ability of anti-NKG2A antibodies to activate NK cells in HNSCC. Effect of a dose-response of cetuximab on NK cells activation was determined by analysis of CD107 and CD137 expression, using as effector cells PBMC freshly isolated from healthy volunteers, and as target cells HNSCC cell lines (FaDu, and H-N), at an E:T ratio of 2.5/1. The read out was CD107 at 4 hours vs. CD137 at 24 hours, using 3 donors (CD107 read out in 4 h) and four donors (CD137 read out in 24 h). Cetuximab was tested at a dose response, ⅒ serial dilution starting at 10 µg/mL. For one healthy volunteer, NK cells were subdivided in NKG2A+ and NKG2A− subsets. Sub-optimal doses of cetuximab were chosen for further testing to explore the effect of an EGFR inhibiting antibody on the ability of anti-NKG2A antibodies to activate NK cells in HNSCC. The 0.001 µg/mL (1 ng/mL) dose is the starting point of the cetuximab effect observed both with CD107 and CD137 readouts. The 0.01 µg/mL (10 ng/mL) dose is approximatively at the EC50 of the cetuximab effect.

The combined effect of anti-NKG2A and a sub-optimal dose of EGFR inhibitor was assessed by analysis of CD107 and CD137 expression, using as effector cells freshly isolated PBMC from healthy volunteers, and as target cells HNSCC cell lines (FaDu, H-N and CAL-27), clones of K562 cell line transfected with HLA-E (Clone E6=HLA-E$^+$, clone F7=HLA-E$^-$), at an E:T ratio of 2.5/1. The read out was CD107 at 4 hours vs. CD137 at 24 hours, using 7 donors (FaDu and H-N)) and two donors (CAL-27).

Anti-NKG2A antibody whose heavy chain amino acid sequence is shown in SEQ ID NO: 3 and whose light chain amino acid sequence is shown in SEQ ID NO: 7 was used at a final concentration of 10 µg/mL corresponding to full functional activity, and EGFR inhibitor cetuximab was used at two suboptimal doses of 0.001 µg/mL or 0.01 µg/mL.

Figure 5:
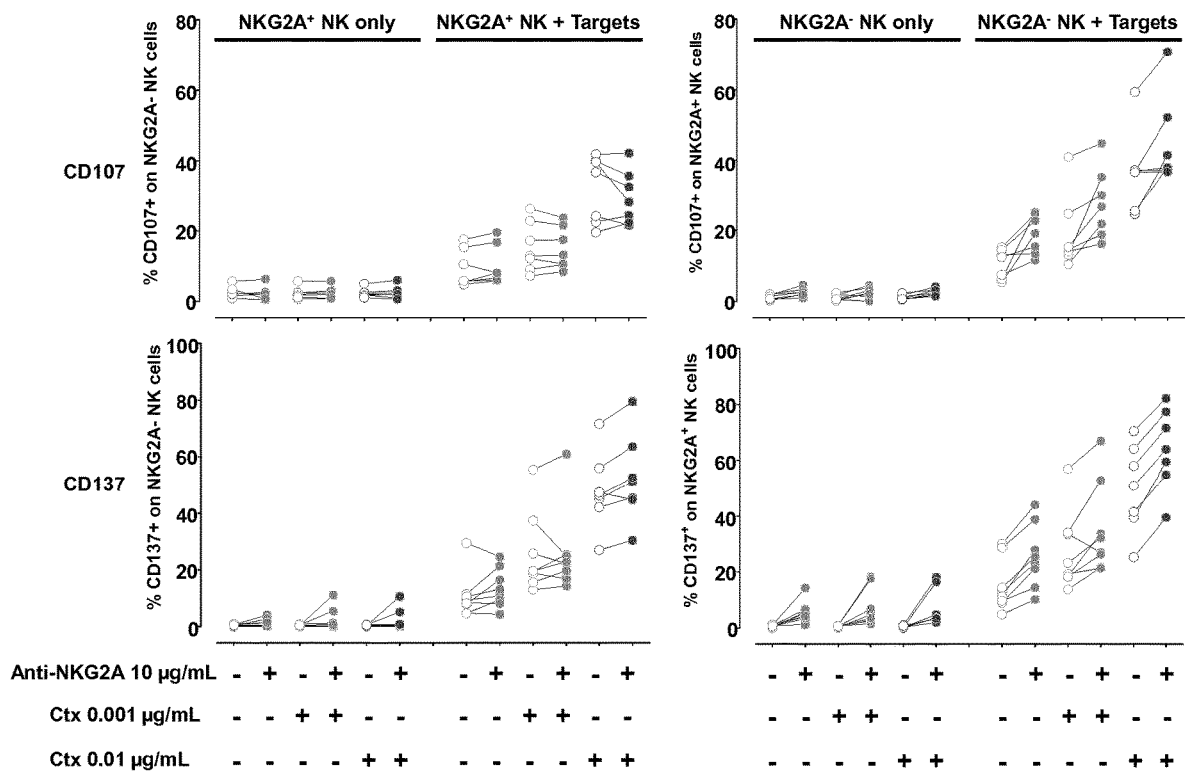
FIG. 5 shows optimal doses of anti-NKG2A enhanced ADCC by NK cells towards HNSCC FaDu cells induced by suboptimal doses of anti-EGFR, cetuximab (ctx).

Full activity concentrations of Anti-NKG2A enhanced ADCC to HNSCC cell lines induced by suboptimal doses of cetuximab. No cetuximab-dependent ADCC was observed on K562 transfected cell lines as they do not express EGF-R. Anti-NKG2A effect is only seen on NKG2A positive NK cells, and is dependent on the level of expression of HLA-E. Indeed, anti-NKG2A effect is seen on cell lines with medium to high HLA-E level of expression (FaDu, CAL-27 and K562-HLA-E clone E6). FIG. 5 is a representative example, shown for FaDu cells. It can be seen in FIG. 5 that full activity doses of anti-NKG2A enhanced ADCC to HNSCC cell lines induced by suboptimal doses of cetuximab (ctx).

Example 11

Combined Effect of Increasing Doses of Anti-NKG2A with Increasing Doses of Cetuximab The effect of the combination of increasing doses of EGFR inhibiting antibody an increasing doses of anti-NKG2A antibodies was evaluated for the ability to activate NK cells toward HNSCC target cells. Experiments sought to evaluate whether anti-NKG2A therapy can still enhance ADCC when cetuximab is used at a saturating dose, and whether the ant-NKG2A effect is dose-dependent.

Briefly, effector cells used were freshly isolated PBMC from healthy volunteers, and target cells were HNSCC cell lines (FaDu, H-N and CAL-27), and clones of K562 cell line transfected with HLA-E (Clone E6=HLA-E$^+$, clone F7=HLA-E$^-$), and an E:T ratio of 2.5/1. The read out was CD107 at 4 hours vs. CD137 at 24 hours, using 2 donors. Anti-NKG2A antibody whose heavy chain amino acid sequence is shown in SEQ ID NO: 3 and whose light chain amino acid sequence is shown in SEQ ID NO: 7 was used at two suboptimal doses of 0.1 and 1 µg/mL, and at a saturating dose of 10 µg/mL. Cetuximab was used at two suboptimal doses of 0.001 µg/mL and 0.01 µg/mL (~EC50) and at a saturating dose of 0.1 µg/mL in these experimental settings.

Figure 6A:
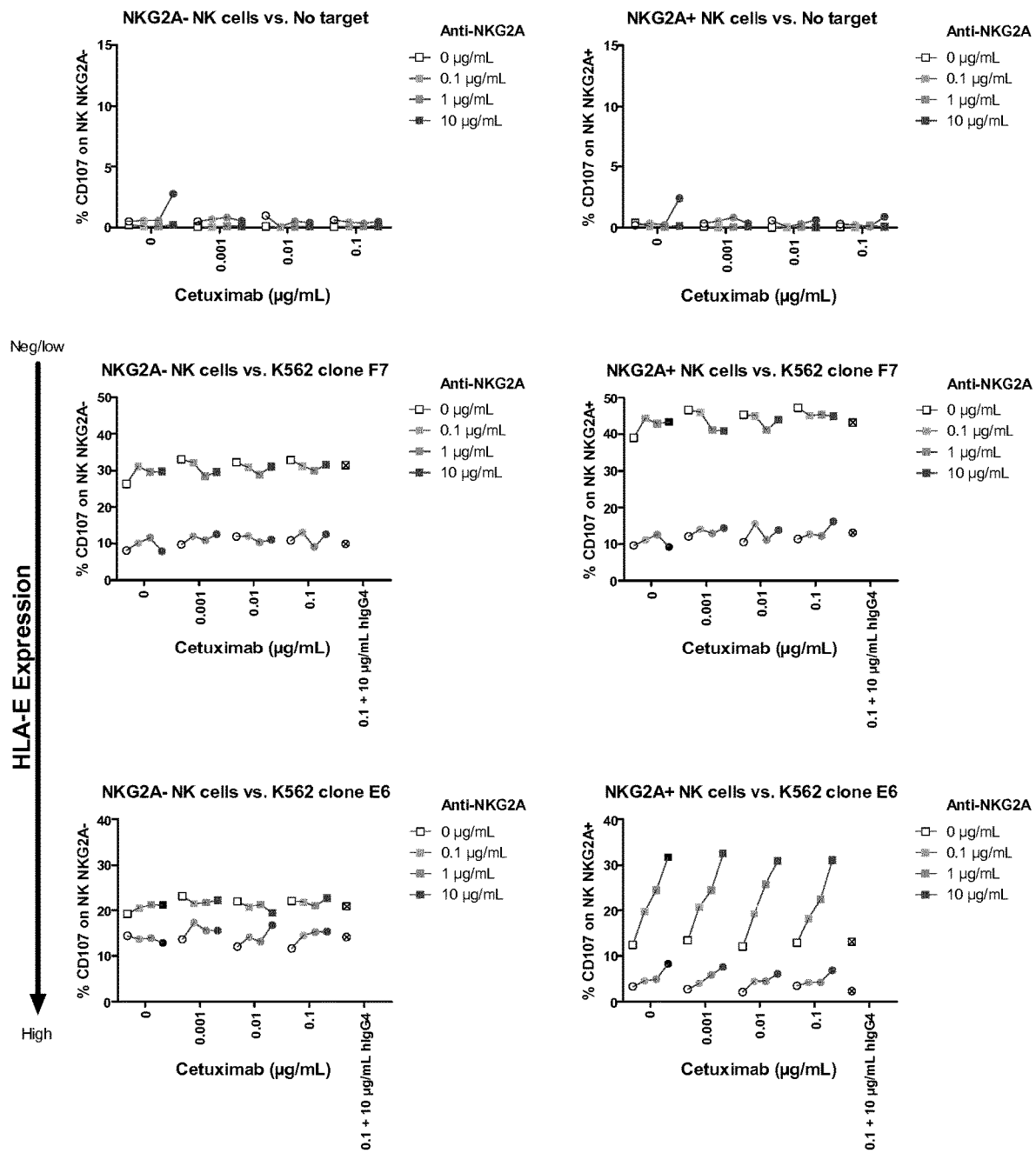
FIGS. 6A and 6B shows effect of increasing doses of anti-NKG2A and increasing doses of anti-EGFR (cetuximab).
Figure 6B:
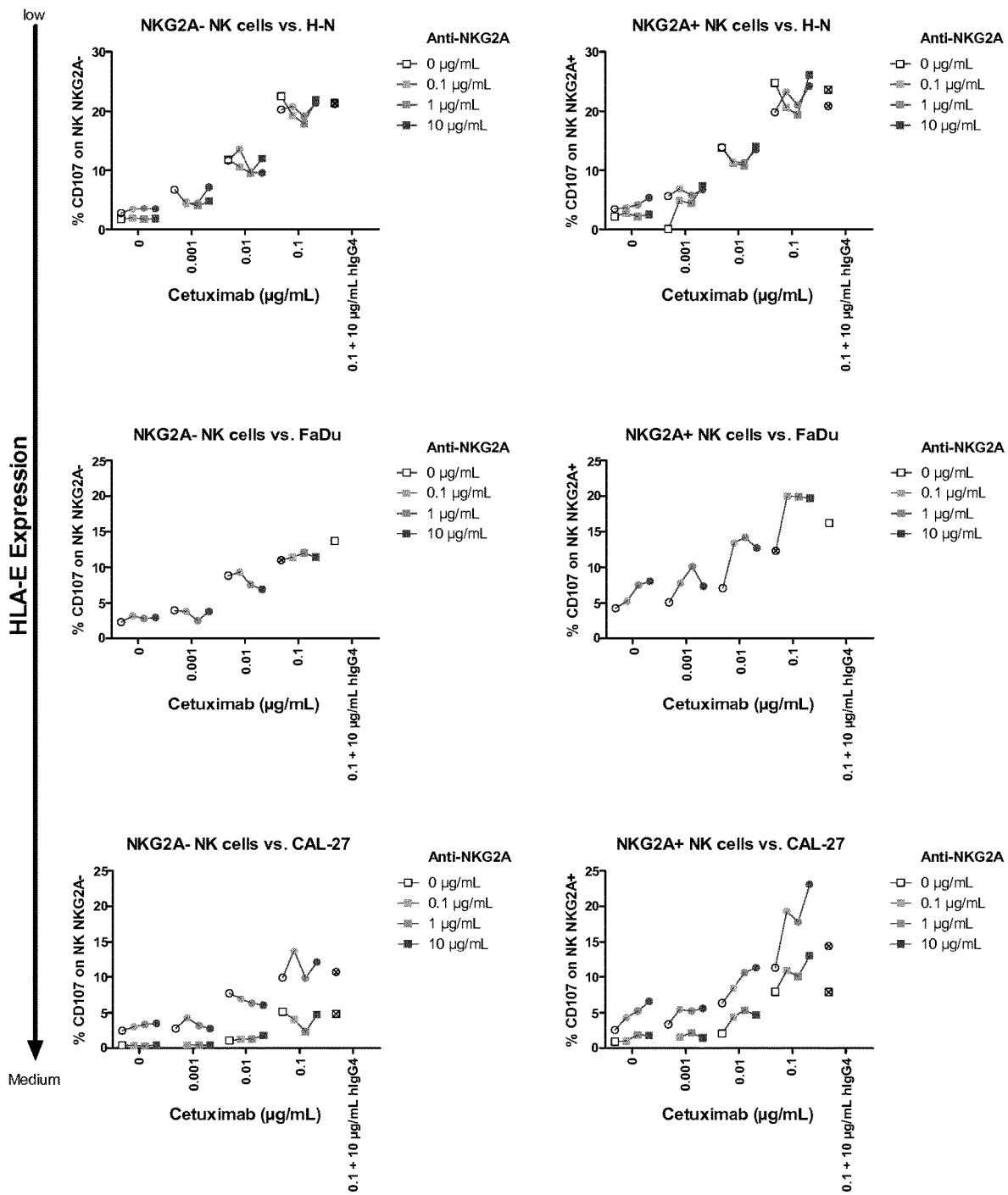

Results are shown in FIGS. 6A and 6B. FIG. 6A shows CD107 read out on controls with no target and with K562-HLA-E transfectants. Each healthy volunteer is represented by a different symbol: squares or circles. Crossed open symbols correspond to condition where anti-NKG2A was replaced by 10 µg/mL hIgG4 isotypic control co-incubated with 0.1 µg/mL cetuximab. It can be seen that the effect of anti-NKG2A antibody is dose-dependent, depends on HLA-E expression level, and is still observed at a saturating dose of cetuximab of 0.1 µg/mL in the clone E6 that expresses HLA-E at high levels. In clone F7 (low HLA-E expression levels), the effect of anti-NKG2A was limited and high doses (e.g. full activity doses) of anti-NKG2A did not further augment the effect.

FIG. 6B shows CD107 read out on HNSCC cell lines. Each healthy volunteer is represented by a different symbol: squares or circles. Crossed open symbols correspond to condition where anti-NKG2A was replaced by 10 µg/mL hIgG4 isotypic control co-incubated with 0.1 µg/mL cetuximab. It can be seen that the effect of anti-NKG2A antibody is dose-dependent, depends on HLA-E expression level, and is still observed at a saturating dose of cetuximab of 0.1 µg/mL in the FaDu or CAL-27 that expresses at higher levels/stain strongly for HLA-E.

The effect of anti-NKG2A antibody is dose-dependent, depends on HLA-E expression level, and is still observed at a saturating dose of cetuximab of 0.1 µg/mL.

Example 12

A human Clinical Trial for Treatment of Cancer with Repeated Injections of Humanized Z270 as Single Agent The primary objective of the trial is to evaluate the antitumor activity of pre-operative IPH2201 (humanized Z270 comprising an S241P mutation) in patients with operable squamous cell carcinoma of the oral cavity. The secondary objectives are to assess the safety of IPH2201, the pharmacokinetics, the immunogenicity and the pharmacodynamics including intra-tumoral biomarkers.

Trial Design:

The trial is a single-center, open label single-arm phase Ib-II study including a run-in part. Previously untreated patients with measurable, clinical intermediate or high risk, stage III or IVa squamous cell carcinoma of the oral cavity will be treated with single agent IPH2201 i.v. every 2 weeks (q2w) for 4 administrations, by intravenous (i.v.) route over 1 hour. The first 6 patients will receive IPH2201 at a dose of 4 mg/kg q2w×4. A minimum interval of one week will be observed between the first administrations of IPH2201 to the 3 first patients treated at 4 mg/kg. The subsequent patients will be treated at a dose of 10 mg/kg q2w×4, the escalation of the dose being allowed by the safety committee after a minimal follow-up of 4 weeks following the first administration in the last patient treated at 4 mg/kg. Standard loco-regional treatment with surgery followed by adjuvant therapy (radiotherapy (RT) or radiochemotherapy (RCT)) according to histopathologic risk factors will be initiated after the last administration of IPH2201. In case of tumor progression loco-regional treatment will be initiated immediately.

Antitumor activity will be assessed clinically and radiologically before the third administration of IPH2201, and 2 weeks after the last administration of IPH2201, before surgery. Tumor measurements will be obtained on target lesions according to RECIST 1.1 criteria. The same imaging techniques will be used for efficacy assessment at baseline and during the preoperative period, for the assessment of the primary end point and/or after surgery, for the monitoring of potential relapses. An assessment by appropriate imaging techniques, at the investigator's discretion (computed tomography (CT) scans and/or Magnetic Resonance Imaging (MRI)) will be performed in all the patients, as well as photographs of the accessible tumor lesions.

A fresh tumor sample will be obtained by biopsy at baseline and the resected specimen will be collected at surgery. Pharmacology (PK/PD) and biomarker studies will be conducted before and after surgery.

The patients will be followed up to one year after the first cycle of administration. After the end of study visit, relapse and survival will be documented post study according to local practices during 2 additional years.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). Where "about" is used in connection with a number, this can be specified as including values corresponding to +/−10% of the specified number.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method of treating an individual having a cancer comprising cancer cells that express HLA-E on their surface with an anti-NKG2A antibody that binds and neutralizes the inhibitory activity of NKG2A, the treatment comprising administering to the individual an antibody comprising a heavy chain comprising an amino acid sequence of any one of SEQ ID NOs: 2-6 and a light chain comprising the amino acid sequence of SEQ ID NO: 7 for at least one administration cycle in which the anti-NKG2A antibody is administered at least twice and in amounts effective to maintain between two successive administrations of the anti-NKG2A antibody a continuous blood concentration of anti-NKG2A antibody of at least 100 µg/ml throughout the treatment cycle.

2. The method of claim 1, wherein the antibody is administered in an amount effective to provide a continuous blood concentration of the anti-NKG2A antibody of at least about 100 µg/ml for at least one week following administration of the anti-NKG2A antibody.

3. The method of claim 1, wherein the antibody is administered 2 times per month.

4. The method of claim 1, wherein the antibody is administered intravenously two times per month and the amount of anti-NKG2A antibody administered is between 6-10 mg/kg body weight.

5. The method of claim 1, wherein the treatment comprises a loading period in which the antibody is administered at least once at an initial dose effective to maintain a blood concentration of at least 100 µg/ml until the next successive administration of the anti-NKG2A antibody, followed by a maintenance period in which the antibody is administered at least twice in a second dose and at a frequency effective to maintain a continuous blood concentration of the anti-NKG2A antibody of at least 100 µg/ml between successive administrations of the anti-NKG2A antibody.

6. The method of claim 5, wherein the antibody is administered intravenously, and wherein the loading period comprises administering the antibody once at a dose of between 8-10 mg/kg, and the maintenance period comprises administering the antibody at least twice, at an interval of about two weeks at dose of between 2-6 mg/kg body weight.

7. The method of claim 1, wherein the individual has a hematological cancer selected from the group consisting of leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma Burketts lymphoma, multiple myeloma, acute myelogenous leukemia, chronic myelogenous leukemia, promyelocytic leukemia, and myelodysplastic syndrome.

8. The method of claim 1, wherein the individual has a solid tumor.

9. The method of claim 8, wherein the individual has a head and neck squamous cell carcinoma (HNSCC).

10. The method of claim 1, wherein the antibody comprises a human IgG4 constant region, wherein the antibody comprises an Fc- engineered constant region comprising an amino acid modification that reduces binding to a human Fcγ receptor, or wherein the antibody fragment lacks an Fc domain.

* * * * *

UNITED STATES PATENT AND TRADEMARK OFFICE
CERTIFICATE OF CORRECTION

PATENT NO. : 10,676,523 B2
APPLICATION NO. : 15/511792
DATED : June 9, 2020
INVENTOR(S) : Pascale Andre et al.

It is certified that error appears in the above-identified patent and that said Letters Patent is hereby corrected as shown below:

On the Title Page

"(72) Inventors: Pascale Andre, Marseilles (FR);
Mathieu Blery, Marseilles (FR);
Carine Paturel, Marcy l'Etoile (FR);
Caroline Soulas, Marseilles (FR);
Nicolaï Wagtmann, Cassis (FR)"

Should read:
--(72) Inventors: Pascale Andre, Marseille (FR);
Mathieu Blery, Marseille (FR);
Carine Paturel, Marcy l'Etoile (FR);
Caroline Soulas, Marseille (FR);
Nicolaï Wagtmann, Cassis (FR)--.

Signed and Sealed this
Third Day of November, 2020

Andrei Iancu
*Director of the United States Patent and Trademark Office*